(12) United States Patent
Bent

(10) Patent No.: US 12,265,079 B1
(45) Date of Patent: Apr. 1, 2025

(54) SYSTEMS AND METHODS FOR DETECTING ANALYTES FROM CAPTURED SINGLE BIOLOGICAL PARTICLES

(71) Applicant: 10x Genomics, Inc., Pleasanton, CA (US)

(72) Inventor: Zachary Bent, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 301 days.

(21) Appl. No.: 17/336,524

(22) Filed: Jun. 2, 2021

Related U.S. Application Data

(60) Provisional application No. 63/033,348, filed on Jun. 2, 2020.

(51) Int. Cl.
  G01N 33/53 (2006.01)
  G01N 33/50 (2006.01)

(52) U.S. Cl.
  CPC ....... *G01N 33/505* (2013.01); *G01N 33/5052* (2013.01); *G01N 33/5308* (2013.01); *G01N 2333/70539* (2013.01)

(58) Field of Classification Search
  CPC ............. G01N 33/505; G01N 33/5052; G01N 33/5308; G01N 2333/70539
  See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,143,496 A | 11/2000 | Brown |

(Continued)

FOREIGN PATENT DOCUMENTS

| | | |
|---|---|---|
| CN | 1680604 | 10/2005 |
| EP | 1923471 | 5/2008 |

(Continued)

OTHER PUBLICATIONS

Pittcon. "Single Molecule Detection of Proteins in Single Cells". News-Medical, Feb. 3, 2017. https://www.news-medical.net/news/20170203/Single-molecule-detection-of-proteins-in-single-cells.aspx. (accessed Oct. 2, 2023) (Year: 2017).*
Kurtulus S, Hildeman D. Assessment of CD4(+) and CD8 (+) T cell responses using MHC class I and II tetramers. Methods Mol Biol. 2013;979:71-9. doi: 10.1007/978-1-62703-290-2_8. PMID: 23397390; PMCID: PMC4265237. (Year: 2013).*
Nam et. al., Science, vol. 301, Issue 5641, pp. 1884-1886, Sep. 26, 2003 (Year: 2003).*
Fattahi et. al., Journal of Cell Communication and Signaling, vol. 11, pp. 97-104, Jan. 24, 2017. (Year: 2017).*
Redmond, D., Poran, A. & Elemento, O. Single-cell TCRseq: paired recovery of entire T-cell alpha and beta chain transcripts in T-cell receptors from single-cell RNAseq. Genome Med 8, 80 (2016). https://doi.org/10.1186/s13073-016-0335-7 (Year: 2016).*

(Continued)

*Primary Examiner* — Carmencita M Belei
(74) *Attorney, Agent, or Firm* — Fish & Richardson P.C.

(57) ABSTRACT

Disclosed are systems and methods for selecting biological particles (e.g., cells or nuclei) based on specific binding to a substrate and single-biological particle measurement of analytes from the substrate-bound biological particles (e.g., cells or nuclei). Single biological particles (e.g., cells or nuclei) from a population of biological particles are captured through their binding to biological particle- (e.g., cell- or nucleus-) and/or molecule-specific biological particle (e.g., cell or nucleus) capture moieties on a substrate. Analytes are released from the single captured biological particles (e.g., cells or nuclei) and bind to analyte-specific barcode molecules associated with the specific biological particle (e.g., cell or nucleus) capture moieties to which a biological particle (e.g., a cell or nucleus) has bound. Analysis of the barcode molecules identifies the bound analytes. The systems and methods are used to select and capture immune cells, such as T-cells that bind specific peptide epitopes through their T-cell receptors (TCRs) or B-cells that bind antigen through their B cell receptors (BCRs). Detection and analysis of barcode molecules that have bound cellular analytes comprising rearranged V(D)J-expressing RNAs from the T-cells or B-cells allows identification of the specific TCR sequences that recognize and bind the specific peptide epitopes or specific BCR sequences that recognize and bind specific antigens.

11 Claims, 10 Drawing Sheets

(56) References Cited

U.S. PATENT DOCUMENTS

| | | |
|---|---|---|
| 6,153,389 A | 11/2000 | Haarer |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,258,568 B1 | 7/2001 | Nyren |
| 6,266,459 B1 | 7/2001 | Walt |
| 6,274,320 B1 | 8/2001 | Rothberg |
| 6,300,063 B1 | 10/2001 | Lipshutz et al. |
| 6,309,824 B1 | 10/2001 | Drmanac |
| 6,344,316 B1 | 2/2002 | Lockhart |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,544,732 B1 | 4/2003 | Chee |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,859,570 B2 | 2/2005 | Walt |
| 6,864,052 B1 | 3/2005 | Drmanac |
| 6,897,023 B2 | 5/2005 | Fu |
| 6,942,968 B1 | 9/2005 | Dickinson et al. |
| 7,057,026 B2 | 6/2006 | Barnes |
| 7,115,400 B1 | 10/2006 | Adessi |
| 7,118,883 B2 | 10/2006 | Inoue |
| 7,166,431 B2 | 1/2007 | Chee et al. |
| 7,211,414 B2 | 5/2007 | Hardin |
| 7,255,994 B2 | 8/2007 | Lao |
| 7,258,976 B2 | 8/2007 | Mitsuhashi |
| 7,297,518 B2 | 11/2007 | Quake |
| 7,329,492 B2 | 2/2008 | Hardin |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,582,420 B2 | 9/2009 | Oliphant et al. |
| 7,601,498 B2 | 10/2009 | Mao |
| 7,635,566 B2 | 12/2009 | Brenner |
| 7,674,752 B2 | 3/2010 | He |
| 7,776,547 B2 | 8/2010 | Roth |
| 7,776,567 B2 | 8/2010 | Mao |
| 7,803,943 B2 | 9/2010 | Mao |
| 7,910,304 B2 | 3/2011 | Drmanac |
| 7,955,794 B2 | 6/2011 | Shen et al. |
| 7,960,119 B2 | 6/2011 | Chee |
| 8,003,354 B2 | 8/2011 | Shen et al. |
| 8,148,068 B2 | 4/2012 | Brenner |
| 8,206,917 B2 | 6/2012 | Chee |
| 8,288,103 B2 | 10/2012 | Oliphant |
| 8,343,500 B2 | 1/2013 | Wraith |
| 8,460,865 B2 | 6/2013 | Chee |
| 8,481,257 B2 | 7/2013 | Van Eijk |
| 8,603,743 B2 | 12/2013 | Liu et al. |
| 8,815,512 B2 | 8/2014 | Van Eijk |
| 8,835,358 B2 | 9/2014 | Fodor |
| 8,911,945 B2 | 12/2014 | Van Eijk |
| 9,062,348 B1 | 6/2015 | Van Eijk |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,404,156 B2 | 8/2016 | Hicks |
| 9,506,061 B2 | 11/2016 | Brown et al. |
| 9,593,365 B2 | 3/2017 | Frisen et al. |
| 9,644,204 B2 | 5/2017 | Hindson et al. |
| 9,694,361 B2 | 7/2017 | Bharadwaj |
| 9,702,004 B2 | 7/2017 | Van Eijk |
| 9,727,810 B2 | 8/2017 | Fodor et al. |
| 9,777,324 B2 | 10/2017 | Van Eijk |
| 9,834,814 B2 | 12/2017 | Peter et al. |
| 9,850,536 B2 | 12/2017 | Oliphant et al. |
| 9,868,979 B2 | 1/2018 | Chee et al. |
| 9,879,313 B2 | 1/2018 | Chee et al. |
| 9,902,950 B2 | 2/2018 | Church et al. |
| 9,975,122 B2 | 5/2018 | Masquelier et al. |
| 10,002,316 B2 | 6/2018 | Fodor et al. |
| 10,011,872 B1 | 7/2018 | Belgrader et al. |
| 10,023,907 B2 | 7/2018 | Van Eijk |
| 10,030,261 B2 | 7/2018 | Frisen et al. |
| 10,053,723 B2 | 8/2018 | Hindson et al. |
| 10,071,377 B2 | 9/2018 | Bharadwaj et al. |
| 10,208,982 B2 | 2/2019 | Bannish et al. |
| 10,266,876 B2 | 4/2019 | Cai et al. |
| 10,267,808 B2 | 4/2019 | Cai |
| 10,273,541 B2 | 4/2019 | Hindson et al. |
| 10,308,982 B2 | 6/2019 | Chee |
| 10,357,771 B2 | 7/2019 | Bharadwaj |
| 10,428,326 B2 | 10/2019 | Belhocine et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,590,244 B2 | 3/2020 | Delaney et al. |
| 10,662,468 B2 | 5/2020 | Chee |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,858,702 B2 | 12/2020 | Lucero et al. |
| 10,872,679 B2 | 12/2020 | Cai et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,001,879 B1 | 5/2021 | Chee |
| 11,008,607 B2 | 5/2021 | Chee |
| 11,008,608 B2 | 5/2021 | Samusik et al. |
| 11,046,996 B1 | 6/2021 | Chee et al. |
| 11,067,567 B2 | 7/2021 | Chee |
| 11,156,603 B2 | 10/2021 | Chee |
| 11,162,132 B2 | 11/2021 | Frisen et al. |
| 11,208,684 B2 | 12/2021 | Chee |
| 11,214,796 B2 | 1/2022 | Shirai et al. |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,459,607 B1 | 10/2022 | Terry et al. |
| 11,479,809 B2 | 10/2022 | Frisen et al. |
| 11,479,810 B1 | 10/2022 | Chee |
| 11,492,612 B1 | 11/2022 | Dadhwal |
| 11,501,440 B2 | 11/2022 | Weisenfeld et al. |
| 11,505,828 B2 | 11/2022 | Chell et al. |
| 11,512,308 B2 | 11/2022 | Gallant et al. |

(56) References Cited

U.S. PATENT DOCUMENTS

| | | |
|---|---|---|
| 11,519,022 B2 | 12/2022 | Chee |
| 11,519,033 B2 | 12/2022 | Schnall-Levin et al. |
| 11,519,138 B2 | 12/2022 | Meier et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,713,480 B2 | 8/2023 | Lee |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 11,981,958 B1 | 5/2024 | Galonska |
| 11,981,960 B1 | 5/2024 | Lin et al. |
| 11,981,965 B2 | 5/2024 | Chell et al. |
| RE50,065 E | 7/2024 | Frisen et al. |
| 12,024,741 B2 | 7/2024 | Tentori et al. |
| 12,031,177 B1 | 7/2024 | Tentori et al. |
| 12,060,604 B2 | 8/2024 | Katiraee et al. |
| 12,071,655 B2 | 8/2024 | Sukovich et al. |
| 12,076,701 B2 | 9/2024 | Bava |
| 12,098,417 B2 | 9/2024 | Engblom et al. |
| 12,098,985 B2 | 9/2024 | Cox et al. |
| 12,110,541 B2 | 10/2024 | Bava |
| 12,117,439 B2 | 10/2024 | Delaney et al. |
| 12,128,403 B2 | 10/2024 | Kim et al. |
| 12,129,516 B2 | 10/2024 | Tentori et al. |
| 12,157,124 B2 | 12/2024 | Cox et al. |
| 12,180,543 B2 | 12/2024 | Uytingco et al. |
| 12,195,790 B2 | 1/2025 | Sukovich et al. |
| 12,203,134 B2 | 1/2025 | Nagendran et al. |
| 12,209,280 B1 | 1/2025 | Mignardi et al. |
| 2002/0040275 A1 | 4/2002 | Cravatt |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0087232 A1 | 5/2003 | Christians |
| 2003/0148335 A1 | 8/2003 | Shen et al. |
| 2003/0162216 A1 | 8/2003 | Gold |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0067492 A1 | 4/2004 | Peng et al. |
| 2004/0096853 A1 | 5/2004 | Mayer |
| 2004/0106110 A1 | 6/2004 | Balasubramanian |
| 2005/0037393 A1 | 2/2005 | Gunderson et al. |
| 2005/0048580 A1 | 3/2005 | Labaer |
| 2005/0100900 A1 | 5/2005 | Kawashima et al. |
| 2005/0118602 A1 | 6/2005 | Li et al. |
| 2005/0130173 A1 | 6/2005 | Leamon et al. |
| 2005/0136414 A1 | 6/2005 | Gunderson et al. |
| 2005/0170373 A1 | 8/2005 | Monforte |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2006/0041385 A1 | 2/2006 | Bauer et al. |
| 2006/0046313 A1 | 3/2006 | Roth |
| 2006/0211001 A1 | 9/2006 | Yu et al. |
| 2006/0216775 A1 | 9/2006 | Burkart et al. |
| 2006/0263789 A1 | 11/2006 | Kincaid |
| 2007/0020640 A1 | 1/2007 | McCloskey et al. |
| 2007/0054288 A1 | 3/2007 | Su et al. |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0009420 A1 | 1/2008 | Schroth et al. |
| 2008/0108804 A1 | 5/2008 | Hayashizaki et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2009/0005252 A1 | 1/2009 | Drmanac et al. |
| 2009/0006002 A1 | 1/2009 | Honisch et al. |
| 2009/0011943 A1 | 1/2009 | Drmanac et al. |
| 2009/0018024 A1 | 1/2009 | Church et al. |
| 2009/0026082 A1 | 1/2009 | Rothberg et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0233802 A1 | 9/2009 | Bignell et al. |
| 2009/0253581 A1 | 10/2009 | Van Eijk et al. |
| 2009/0270273 A1 | 10/2009 | Burns et al. |
| 2009/0289184 A1 | 11/2009 | Deininger |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0120097 A1 | 5/2010 | Matz et al. |
| 2010/0120098 A1 | 5/2010 | Grunenwald et al. |

(56) References Cited

U.S. PATENT DOCUMENTS

| | | |
|---|---|---|
| 2010/0145037 A1 | 6/2010 | Brive et al. |
| 2011/0028685 A1 | 2/2011 | Purkayastha et al. |
| 2011/0059436 A1 | 3/2011 | Hardin et al. |
| 2011/0223613 A1 | 9/2011 | Gut |
| 2011/0245111 A1 | 10/2011 | Chee |
| 2012/0010091 A1 | 1/2012 | Linnarson |
| 2012/0135871 A1 | 5/2012 | van Eijk et al. |
| 2012/0202698 A1 | 8/2012 | van Eijk et al. |
| 2014/0065609 A1 | 3/2014 | Hicks et al. |
| 2014/0066318 A1 | 3/2014 | Frisen et al. |
| 2014/0099637 A1 | 4/2014 | Nolan et al. |
| 2014/0155295 A1 | 6/2014 | Hindson et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0378350 A1 | 12/2014 | Hindson et al. |
| 2015/0132743 A1 | 5/2015 | Egidio et al. |
| 2015/0292988 A1 | 10/2015 | Bharadwaj et al. |
| 2015/0298091 A1 | 10/2015 | Weitz et al. |
| 2015/0344942 A1 | 12/2015 | Frisen et al. |
| 2015/0368704 A1 | 12/2015 | Fan et al. |
| 2015/0376609 A1 | 12/2015 | Hindson et al. |
| 2016/0032282 A1 | 2/2016 | Vigneault et al. |
| 2016/0138091 A1 | 5/2016 | Chee et al. |
| 2016/0145677 A1 | 5/2016 | Chee et al. |
| 2016/0201125 A1 | 7/2016 | Samuels et al. |
| 2016/0253584 A1 | 9/2016 | Fodor et al. |
| 2016/0289669 A1 | 10/2016 | Fan et al. |
| 2016/0289740 A1 | 10/2016 | Fu et al. |
| 2016/0298180 A1 | 10/2016 | Chee |
| 2017/0159109 A1 | 6/2017 | Zheng et al. |
| 2017/0220733 A1 | 8/2017 | Zhuang et al. |
| 2017/0242020 A1 | 8/2017 | Yamauchi et al. |
| 2017/0342405 A1 | 11/2017 | Fu et al. |
| 2017/0343545 A1 | 11/2017 | Hadrup et al. |
| 2018/0057873 A1 | 3/2018 | Zhou et al. |
| 2018/0080019 A1 | 3/2018 | Blainey et al. |
| 2018/0088112 A1 | 3/2018 | Fan et al. |
| 2018/0105808 A1 | 4/2018 | Mikkelsen et al. |
| 2018/0112212 A1 | 4/2018 | Nicol et al. |
| 2018/0112261 A1 | 4/2018 | Van Driel et al. |
| 2018/0114316 A1 | 4/2018 | Lele et al. |
| 2018/0201980 A1 | 7/2018 | Chee et al. |
| 2018/0216162 A1 | 8/2018 | Belhocine et al. |
| 2018/0245142 A1 | 8/2018 | So et al. |
| 2018/0251825 A1 | 9/2018 | Stoeckius et al. |
| 2018/0282803 A1 * | 10/2018 | Belgrader ............... C12Q 1/683 |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0334670 A1 | 11/2018 | Bharadwaj et al. |
| 2018/0346970 A1 | 12/2018 | Chang |
| 2019/0064173 A1 | 2/2019 | Bharadwaj et al. |
| 2019/0085324 A1 | 3/2019 | Regev et al. |
| 2019/0144936 A1 | 5/2019 | Gierahn et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0203275 A1 | 7/2019 | Frisen et al. |
| 2019/0218607 A1 | 7/2019 | Love et al. |
| 2019/0233878 A1 | 8/2019 | Delaney et al. |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0276880 A1 | 9/2019 | Fan et al. |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0338353 A1 | 11/2019 | Belgrader et al. |
| 2019/0352708 A1 | 11/2019 | Gaige et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0002764 A1 | 1/2020 | Belgrader et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0109443 A1 | 4/2020 | Chee |
| 2020/0173985 A1 | 6/2020 | Dong et al. |
| 2020/0217850 A1 | 7/2020 | Liu et al. |
| 2020/0256867 A1 | 8/2020 | Hennek et al. |
| 2020/0277663 A1 | 9/2020 | Iyer |
| 2020/0277664 A1 | 9/2020 | Frenz |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |

(56) References Cited

U.S. PATENT DOCUMENTS

| | | |
|---|---|---|
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0315984 A1 | 10/2022 | Edelman et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403374 A1 | 12/2022 | Soumillon |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0416807 A1 | 1/2023 | Chee |
| 2023/0416808 A1 | 1/2023 | Sukovich et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0267625 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304072 A1 | 9/2023 | Gohil et al. |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0351619 A1 | 11/2023 | Tentori et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0018589 A1 | 1/2024 | Schnall-Levin et al. |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |

(56) References Cited

U.S. PATENT DOCUMENTS

| | | |
|---|---|---|
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |
| 2024/0182968 A1 | 6/2024 | Bava |
| 2024/0191286 A1 | 6/2024 | Boutet et al. |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |
| 2024/0219701 A1 | 7/2024 | Tentori et al. |
| 2024/0253036 A1 | 8/2024 | Kim et al. |
| 2024/0263218 A1 | 8/2024 | Katiraee et al. |
| 2024/0271190 A1 | 8/2024 | Stoeckius et al. |
| 2024/0271195 A1 | 8/2024 | Mikhaiel et al. |
| 2024/0279747 A1 | 8/2024 | Williams |
| 2024/0287600 A1 | 8/2024 | Iyer et al. |
| 2024/0294971 A1 | 9/2024 | Galonska |
| 2024/0294974 A1 | 9/2024 | Galonska et al. |
| 2024/0294975 A1 | 9/2024 | Lin et al. |
| 2024/0301488 A1 | 9/2024 | Stoeckius |
| 2024/0301489 A1 | 9/2024 | Chew et al. |
| 2024/0360494 A1 | 10/2024 | Costa et al. |
| 2024/0368711 A1 | 11/2024 | Giacomello et al. |
| 2024/0377297 A1 | 11/2024 | Cox et al. |
| 2024/0385088 A1 | 11/2024 | Kim et al. |
| 2024/0392349 A1 | 11/2024 | Frisen et al. |
| 2024/0392351 A1 | 11/2024 | Chee |
| 2024/0392352 A1 | 11/2024 | Stahl et al. |
| 2024/0392353 A1 | 11/2024 | Engblom et al. |
| 2024/0401109 A1 | 12/2024 | Kim et al. |
| 2024/0401117 A1 | 12/2024 | Bava |
| 2024/0401118 A1 | 12/2024 | Tentori et al. |
| 2024/0404301 A1 | 12/2024 | Li et al. |
| 2024/0408593 A1 | 12/2024 | Kim et al. |
| 2024/0416315 A1 | 12/2024 | Bava |
| 2024/0417783 A1 | 12/2024 | Chew et al. |
| 2024/0417784 A1 | 12/2024 | Sukovich et al. |
| 2025/0002980 A1 | 1/2025 | Tentori et al. |
| 2025/0002982 A1 | 1/2025 | Stoeckius et al. |
| 2025/0003956 A1 | 1/2025 | Delaney et al. |
| 2025/0019689 A1 | 1/2025 | Galonska et al. |
| 2025/0019749 A1 | 1/2025 | Katiraee et al. |

FOREIGN PATENT DOCUMENTS

| | | |
|---|---|---|
| EP | 2002017 | 12/2008 |
| EP | 2130913 | 12/2009 |
| EP | 2881465 | 6/2015 |
| EP | 3013984 | 5/2016 |
| EP | 3511423 | 7/2019 |
| EP | 3541956 | 9/2019 |
| RU | 2270254 | 2/2006 |
| WO | WO 1989/010977 | 11/1989 |
| WO | WO 1991/006678 | 5/1991 |
| WO | WO 1995/025116 | 9/1995 |
| WO | WO 1995/035505 | 12/1995 |
| WO | WO 2000/017390 | 3/2000 |
| WO | WO 2000/024940 | 5/2000 |
| WO | WO 2000/063437 | 10/2000 |
| WO | WO 2002/024952 | 3/2002 |
| WO | WO 2002/059355 | 8/2002 |
| WO | WO 2002/077283 | 10/2002 |
| WO | WO 2003/002979 | 1/2003 |
| WO | WO 2003/010176 | 2/2003 |
| WO | WO 2005/007814 | 1/2005 |
| WO | WO 2006/117541 | 11/2006 |
| WO | WO 2007/073171 | 6/2007 |
| WO | WO 2007/076726 | 7/2007 |
| WO | WO 2007/145612 | 12/2007 |
| WO | WO 2008/075086 | 6/2008 |
| WO | WO 2009/032167 | 3/2009 |
| WO | WO 2009/152928 | 12/2009 |
| WO | WO 2010/088517 | 8/2010 |
| WO | WO 2010/126614 | 11/2010 |
| WO | WO 2011/008502 | 1/2011 |
| WO | WO 2011/068088 | 6/2011 |
| WO | WO 2011/094669 | 8/2011 |
| WO | WO 2012/048341 | 4/2012 |
| WO | WO 2012/083225 | 6/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/150082 | 10/2013 |
| WO | WO 2013/150083 | 10/2013 |
| WO | WO 2014/060483 | 4/2014 |
| WO | WO 2014/201273 | 12/2014 |
| WO | WO 2014/210223 | 12/2014 |
| WO | WO 2015/031691 | 3/2015 |
| WO | WO 2015/168161 | 11/2015 |
| WO | WO 2015/188839 | 12/2015 |
| WO | WO 2016/040476 | 3/2016 |
| WO | WO 2016/057552 | 4/2016 |
| WO | WO 2016/126871 | 8/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2017/013170 | 1/2017 |
| WO | WO 2017/019456 | 2/2017 |
| WO | WO 2017/075265 | 5/2017 |
| WO | WO 2017/075293 | 5/2017 |
| WO | WO 2017/096158 | 7/2017 |
| WO | WO 2017/147483 | 8/2017 |
| WO | WO 2018/064640 | 4/2018 |
| WO | WO 2018/075693 | 4/2018 |
| WO | WO 2018/091676 | 5/2018 |
| WO | WO 2018/175779 | 9/2018 |
| WO | WO 2019/104337 | 5/2019 |
| WO | WO 2019/113457 | 6/2019 |
| WO | WO 2019/113533 | 6/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047004 | 3/2020 |
| WO | WO 2020/047005 | 3/2020 |
| WO | WO 2020/047007 | 3/2020 |
| WO | WO 2020/047010 | 3/2020 |
| WO | WO 2020/076979 | 4/2020 |
| WO | WO 2020/077236 | 4/2020 |
| WO | WO 2020/099640 | 5/2020 |
| WO | WO 2020/123301 | 6/2020 |
| WO | WO 2020/123305 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/227309 | 11/2020 |
| WO | WO 2020/243579 | 12/2020 |
| WO | WO 2021/041974 | 3/2021 |
| WO | WO 2021/067246 | 4/2021 |
| WO | WO 2021/067514 | 4/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |

(56) References Cited

FOREIGN PATENT DOCUMENTS

| | | |
|---|---|---|
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |

OTHER PUBLICATIONS

Tang, F., Barbaciroru, C., Wang, Y et al. mRNA-Seq whole-transcriptome analysis of a single cell. Nat Methods 6, 377-382 (2009). https://doi.org/10.1038/nmeth.1315 (Year: 2009).*
U.S. Appl. No. 16/353,937, filed Mar. 14, 2019, Frisen et al.
U.S. Appl. No. 17/707,189, filed Mar. 29, 2022, Chell et al.
U.S. Appl. No. 63/033,348, filed Jun. 2, 2020, Bent.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.
Adamson et al., "A Multiplexed Single-Cell CRISPR Screening Platform Enables Systematic Dissection of the Unfolded Protein Response," Cell, Dec. 2016, 167(7):1867-1882.e21.
Adessi et al., "Solid phase DNA amplification: characterisation of primer attachment and amplification mechanisms," Nucl. Acids Res., 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Anderson et al., "Microarrayed Compound Screening to Identify Activators and Inhibitors of AMP-Activated Protein Kinase," J. of Biomolecular Screening, 2004, 9:112.
Andersson et al., "Analysis of protein expression in cell microarrays: a tool for antibody-based proteomics.," J Histochem Cytochem., 4(12): 1413-1423, 2006.
Armani et al., "2D-PCR: a method of mapping DNA in tissue sections," Lab Chip, 2009, 9(24):3526-34.
Asp et al., "Spatially Resolved Transcriptomes—Next Generation Tools for Tissue Exploration," Bioessays, Oct. 2020, 42(10):e1900221, 16 pages.

(56) References Cited

OTHER PUBLICATIONS

Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Azioune et al., "Simple and rapid process for single cell micropatterning," Lab Chip, Jun. 2009, 9(11):1640-1642.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell Cut&Tag profiles histone modifications and transcription factors in complex tissues," Nat Biotechnol., Jul. 2021, 39(7):825-835, Abstract.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bergenståhle et al., "Seamless integration of image and molecular analysis for spatial transcriptomics workflows," BMC Genomics, Jul. 2020, 21(1):482, 7 pages.
Bielas et al., "Quantification of random genomic mutations," Nat. Methods, 2005, 2(4):285-290.
Biosyntagma.com, [online], "Resolving Heterogeneity One Cell at a Time," available on or before Apr. 21, 2017, via Internet Archive: Wayback Machine URL<https://web.archive.org/web/20170421212315/http:/www.biosyntagma.com/>, retrieved on Sep. 29, 2021, URL<http://www.biosyntagma.com/>, 3 pages.
Birney et al., "Identification and analysis of functional elements in 1% of the human genome by the Encode pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4, " Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections, " Biotechniques, 1998, 24(1):92-100.
Butler et al., "Integrating single-cell transcriptomic data across different conditions, technologies, and species," Nat Biotechnol., Jun. 2018, 36(5):411-420.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "ATAC-see reveals the accessible genome by transposase-mediated imaging and sequencing," Nature Methods, Dec. 2016, 13(12):1013-1020.
Chen et al., "Geometric control of cell life and death," Science, May 1997, 276(5317):1425-1428.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "µCB-seq: microfluidic cell barcoding and sequencing for high-resolution imaging and sequencing of single cells," Lab Chip, Nov. 2020, 20(21):3899-3913.
Cheng et al., "Sensitive Detection of Small Molecules by Competitive Immunomagnetic-Proximity Ligation Assay," Anal Chem, 2012, 84:2129-2132.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Chung et al., "Imaging single-cell signaling dynamics with a deterministic high-density single-cell trap array," Anal Chem, Sep. 2011, 83(18):7044-7052.
Chung et al., "Structural and molecular interrogation of intact biological systems," Nature, May 2013, 497:332-337.
Codeluppi et al., "Spatial organization of the somatosensory cortex revealed by osmFISH," Nature Methods, Nov. 2018, 15:932-935.
Collins et al., "Two-dimensional single-cell patterning with one cell per well driven by surface acoustic waves," Nature Communications, Nov. 2015, 6:8686, 11 pages.
Constantine et al., "Use of genechip high-density oligonucleotide arrays for gene expression monitoring," Life Science News, Amersham Life Science, 1998, pp. 11-14.
Corces et al., "Lineage-specific and single-cell chromatin accessibility charts human hematopoiesis and leukemia evolution," Nature Genetics, Oct. 2016, 48(10):1193-1203.
Crosetto et al., "Spatially resolved transcriptomics and beyond," Nature Review Genetics, 2015, 16(1):57-66.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Datlinger et al., "Pooled CRISPR screening with single-cell transcriptome readout," Nat Methods, Mar. 2017, 14(3):297-301.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dean et al., "Comprehensive human genome amplification using multiple displacement amplification," Proc Natl. Acad. Sci. USA, 2002, 99(8):5261-66.

(56) References Cited

OTHER PUBLICATIONS

Depasquale et al., "DoubletDecon: Deconvoluting Doublets from Single-Cell RNA-Sequencing Data," Cell Rep., Nov. 5, 2019, 29(6):1718-1727.e8, 19 pages.
Ding et al., "On-chip manipulation of single microparticles, cells, and organisms using surface acoustic waves," PNAS, Jul. 2012, 109(28):11105-11109.
Dixit et al., "Perturb-Seq: Dissecting Molecular Circuits with Scalable Single-Cell RNA Profiling of Pooled Genetic Screens," Cell, Dec. 2016, 167(7):1853-1866.e17.
Duncan et al., "Affinity chromatography of a sequence-specific DNA binding protein using Teflon-linked oligonucleotides," Anal. Biochem., 1988, 169(1):104-108.
Eberwine et al., "Analysis of gene expression in single live neurons," Proc. Natl. Acad. Sci., USA 89, 3010-3014, 1992.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Transcriptome-scale super-resolved imaging in tissues by RNA seqFISH+," Nature, Apr. 2019, 568(7751):235-239, 37 pages.
Falconnet et al., "Surface engineering approaches to micropattern surfaces for cell-based assays," Biomaterials, Jun. 2006, 27(16):3044-3063.
Fire et al., "Rolling replication of short DNA circles, " Proc. Natl. Acad. Sci., 1995, 92(10):4641-4645.
Fodor et al., "Light-directed, spatially addressable parallel chemical synthesis," Science, 1995, 251(4995):767-773.
Folch et al., "Microfabricated elastomeric stencils for micropatterning cell cultures," J Biomed Mater Res, Nov. 2000, 52(2):346-353.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gene@arrays[online], BeadArray Technology, available on or before Feb. 14, 2015, via Internet Archive: Wayback Machine URL <https://web.archive.org/web/20150214084616/http://geneaarrays.com/services/microarrays/illumina/beadarray-technology/>, [retrieved on Jan. 30, 2020], 3 pages.
Giam et al., "Scanning probe-enabled nanocombinatorics define the relationship between fibronectin feature size and stem cell fate," PNAS, Mar. 2012, 109(12):4377-4382.
Gierahn et al., "Seq-Well: portable, low-cost RNA sequencing of single cells at high throughput," ResearchSquare, 2017, 53 pages.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-Fish," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Gracia Villacampa et al., "Genome-wide Spatial Expression Profiling in FFPE Tissues," bioRxiv, 2020, pp. 38 pages.
Gross et al., "Technologies for Single-Cell Isolation," Int. J Mol. Sci., Jul. 2015, 16(8):16897-16919.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Habib et al., "Div-Seq: Single-nucleus RNA-Seq reveals dynamics of rare adult newborn neurons," Science, Aug. 2016, 353(6302):925-8.
Habib et al., "Massively parallel single-nucleus RNA-seq with DroNc-seq," Nat Methods, Oct. 2017, 14(10):955-958.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hammond et al., "Profiling cellular protein complexes by proximity ligation with dual tag microarray readout," PLoS One, 2012, 7(7):e40405, 9 pages.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He, "Cell-free protein synthesis: applications in proteomics and biotechnology," New Biotechnology, 2008, 25(2-3):126-132.
Heaton et al., "Souporcell: Robust clustering of single cell RNAseq by genotype and ambient RNA inference without reference genotypes," bioRxiv, Sep. 2019, 22 pages.
Hedskog et al., "Dynamics of HIV-1 Quasispecies during Antiviral Treatment Dissected using Ultra-Deep Pyrosequencing," PLoS One, 5(7): e11345, 2010.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Hu et al., "Dissecting Cell-Type Composition and Activity-Dependent Transcriptional State in Mammalian Brains by Massively Parallel Single-Nucleus RNA-Seq," Mol Cell., Dec. 2017, 68(5):1006-1015.
Hughes et al., "Highly Efficient, Massively-Parallel Single-Cell RNA-Seq Reveals Cellular States and Molecular Features of Human Skin Pathology," bioRxiv, Jul. 2019, 51 pages.
Jabara et al., Accurate sampling and deep sequencing of the HIV-1 protease gene using a Primer ID. PNAS 108(50); 20166-20171, 2011.
Jaitin et al., "Dissecting Immune Circuits by Linking CRISPR-Pooled Screens with Single-Cell RNA-Seq," Cell, Dec. 2016, 167(7):1883-1896.e15.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jones et al., "Comparative lesion sequencing provides insights into tumor evolution," Proc. Natl. Acad. Sci. USA, 105(11): 4283-4288, 2008.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Kaya-Okur et al., "Cut&Tag for efficient epigenomic profiling of small samples and single cells," Apr. 2019, 10(1):1930, 10 pages.
Korbel et al., "Paired-end mapping reveals extensive structural variation in the human genome," Science, 2007, 318(5849):420-426.
Korsunsky et al., "Fast, sensitive and accurate integration of single-cell data with Harmony," Nat. Methods, Dec. 2019, 16(12):1289-1296.

(56) References Cited

OTHER PUBLICATIONS

Kozlov et al., "A highly scalable peptide-based assay system for proteomics," PLoS One, 2012, 7(6):e37441, 10 pages.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lacar et al., "Nuclear RNA-seq of single neurons reveals molecular signatures of activation," Nat Commun., Apr. 2016, 7:11022, 12 pages.
Lage et al., "Whole genome analysis of genetic alterations in small DNA samples using hyperbranched strand displacement amplification and array-CGH," Genome Research, 2003, 13(2):294-307.
Lake et al., "Neuronal subtypes and diversity revealed by single-nucleus RNA sequencing of the human brain," Science, Jun. 2016, 352(6293):1586-90.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Laurell et al., "Chip integrated strategies for acoustic separation and manipulation of cells and particles," Chem. Soc. Rev., Mar. 2007, 36(3):492-506.
Lee et al., "XYZeq: Spatially resolved single-cell RNA sequencing reveals expression heterogeneity in the tumor microenvironment," Science Advances, 2021, 7:eabg4755, 1-14.
Leriche et al., "Cleavable linkers in chemical biology," Bioorganic & Medicinal Chemistry, 2012, 20:571-582.
Liberali et al., "Single-cell and multivariate approaches in genetic perturbation screens," Nat Rev Genet., Jan. 2015, 16(1):18-32.
Lin et al., "Microfluidic cell trap array for controlled positioning of single cells on adhesive micropatterns," Lab Chip, Feb. 2013, 13(4):714-721.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omnics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lubeck et al., "Single cell systems biology by super-resolution imaging and combinatorial labeling," Nature Methods, Jan. 2013, 9(7):743-748, 18 pages.
Lubeck et al., "Single-cell in situ RNA profiling by sequential hybridization," Nature Methods, Apr. 2014, 11(4):360-361, 2 pages (Supplemental Materials).
Lundberg et al., "Multiplexed homogeneous proximity ligation assays for high-throughput protein biomarker research in serological material," Mol Cell Proteomics, 2011, 10(4):M110.004978, 11 pages.
Macbeath et al., "Printing proteins as microarrays for high-throughput function determination," Science, Sep. 2000, 289(5485):1760-1763.
Macosko et al., "Highly Parallel Genome-wide Expression Profiling of Individual Cells Using Nanoliter Droplets," Cell, 2015, 161:1202-1214.
Madissoon et al., "scRNA-seq assessment of the human lung, spleen, and esophagus tissue stability after cold preservation," Genome Biol., Dec. 2019, 21(1):1, 16 pages.
McGinnis et al., "Multi-seq: sample multiplexing for single-cell RNA sequencing using lipid-tagged indices," Nat Methods, Jul. 2019, 16(7): 619-626, 14 pages.
Meers et al., "Improved Cut&Run chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mizusawa et al., "A bacteriophage lambda vector for cloning with BamHI and Sau3A," Gene, 1982, 20(3):317-322.
Mortazavi et al., "Mapping and quantifying mammalian transcriptomes by RNA-Seq," Nature Methods, 5(7): 621-8, 2008.
Nakamura et al., "Biocompatible inkjet printing technique for designed seeding of individual living cells," Tissue Eng, Nov. 2005, 11(11-12):1658-1666.
Nam et al., "Somatic mutations and cell identity linked by Genotyping of Transcriptomes," Nature, Jul. 2019, 571(7765):355-360.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Nikiforov et al., "The use of 96-well polystyrene plates for DNA hybridization-based assays: an evaluation of different approaches to oligonucleotide immobilization," Anal Biochem, May 1995, 227(1):201-9.
Nowak et al., "Entering the Postgenome Era," Science, 1995, 270(5235):368-71.
Ostuni et al., "Patterning Mammalian Cells Using Elastomeric Membranes," Langmuir, Aug. 2000, 16(20):7811-7819.
PCT International Preliminary Report on Patentability in International Appln. No. PCT/EP2016/057355, dated Oct. 10, 2017, 7 pages.
PCT International Preliminary Report on Patentability in International Appln. No. PCT/US2021/018795, dated Sep. 1, 2022, 10 pages.
PCT International Preliminary Report on Patentability in International Appln. No. PCT/US2021/018816, dated Sep. 1, 2022, 9 pages.
PCT International Search Report and Written Opinion in International Appln. No. PCT/US2022/028071, dated Aug. 25, 2022, 13 pages.
Pemov et al., "DNA analysis with multiplex microarray-enhanced PCR," Nucl. Acids Res., Jan. 2005, 33(2):e11, 9 pages.
Perler et al., "Intervening sequences in an Archaea DNA polymerase gen," Proc Natl Acad Sci USA, Jun. 1992, 89(12):5577-5581.
Petterson et al., "Generations of sequencing technologies," Genomics, 2009, 93(2):105-111.
Picelli et al., "Full-length RNA-seq from single cells using Smartseq2," Nat Protoc., Jan. 2014, 9(1):171-81.
Polsky-Cynkin et al., "Use of DNA immobilized on plastic and agarose supports to detect DNA by sandwich hybridization," Clin. Chem., 1985, 31(9):1438-1443.
Ranki et al., "Sandwich hybridization as a convenient method for the detection of nucleic acids in crude samples," Gene, 1983, 21(1-2):77-85.

(56) References Cited

OTHER PUBLICATIONS

Reinartz et al., "Massively parallel signature sequencing (MPSS) as a tool for in-depth quantitative gene expression profiling in all organisms," Brief Funct Genomic Proteomic, Feb. 2002, 1(1):95-104.
Rettig et al., "Large-scale single-cell trapping and imaging using microwell arrays," Anal Chem, Sep. 2005, 77(17):5628-5634.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Rosenthal et al., "Cell patterning chip for controlling the stem cell microenvironment," Biomaterials, Jul. 2007, 28(21):3208-3216.
Salmén et al., "Barcoded solid-phase RNA capture for Spatial Transcriptomics profiling in mammalian tissue sections," Nature Protocols, Oct. 2018, 13(11):2501-2534.
Satpathy et al., "Massively parallel single-cell chromatin landscapes of human immune cell development and intratumoral T cell exhaustion," Nat Biotechnol., Aug. 2019, 37(8):925-936.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Shalon et al., "A DNA microarray system for analyzing complex DNA samples using two-color fluorescent probe hybridization," Genome Res., Jul. 1996, 6(7):639-45.
Shirai et al., "Novel Tools for Analyzing Gene Expressions in Single Cells," The 5th International Workshop on Approaches to Single-Cell Analysis, The University of Tokyo, Mar. 3-4, 2011, 1 page.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Sountoulidis et al., "SCRINSHOT, a spatial method for single-cell resolution mapping of cell states in tissue sections," PLoS Biol., Nov. 2020, 18(11):e3000675, 32 pages.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoeckius et al., "Cell Hashing with barcoded antibodies enables multiplexing and doublet detection for single cell genomics," Genome Biology, Dec. 19, 2018, 19: 224, 12 pages.
Strell et al., "Placing RNA in context and space—methods for spatially resolved transcriptomics," The FEBS Journal, 2019, 286(8):1468-1481.
Stuart et al., "Comprehensive Integration of Single-Cell Data," Cell, Jun. 2019, 177(7):1888-1902.
Suh et al., "A simple soft lithographic route to fabrication of poly(ethylene glycol) microstructures for protein and cell patterning," Biomaterials, Feb. 2004, 25(3):557-563.
Takei et al., "Integrated Spatial Genomics Reveals Global Architecture Of Single Nuclei," Nature, Jan. 27, 2021, 590(7845):344-350, 53 pages.
Tan et al., "Parylene peel-off arrays to probe the role of cell-cell interactions in tumour angiogenesis," Integr Biol (Camb), Oct. 2009, 1(10):587-594.
Tang et al., "RNA-Seq analysis to capture the transcriptome landscape of a single cell.," Nat Protoc., 5:516-35, 2010.
Taniguchi et al., "Quantitative analysis of gene expression in a single cell by qPCR," Nature Methods, 6, pp. 503-506, 2009.
Tentori et al., "Detection of Isoforms Differing by a Single Charge Unit in Individual Cells," Chem. Int. Ed., 2016, 55(40):12431-5.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tseng et al., "Magnetic nanoparticle-mediated massively parallel mechanical modulation of single-cell behavior," Nat Methods, Nov. 2012, 9(11):1113-1119.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vermesh et al., "High-density, multiplexed patterning of cells at single-cell resolution for tissue engineering and other applications," Angew Chem Int Ed Engl, Aug. 2011, 50(32):7378-7380.
Vickovic et al., "High-definition spatial transcriptomics for in situ tissue profiling," Nat Methods, Oct. 2019, 16(10):987-990.
Vickovic et al., "Massive and parallel expression profiling using microarrayed single-cell sequencing," Nature Communications, 2016, 7(13182):1-9.
Vickovic et al., "SM-Omics: An automated Platform for High-Throughput Spatial Multi-Omics," bioRxiv, Oct. 2020, 40 pages.
Vogelstein et al., "Digital PCR," Proceedings of the National Academy of Sciences, Aug. 1999, 96(16):9236-9241.
Walker et al., "Strand displacement amplification—an isothermal, in vitro DNA amplification technique," Nucleic Acids Research, 1992, 20(7):1691-1696.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Single cell analysis: the new frontier in 'omics,'" Trends Biotechnol., 28: 281-90, 2010.
Wheeler et al., "Microfluidic device for single-cell analysis," Analytical Chemistry, Jul. 2003, 75(14):3581-3586.
Wood et al., "Single cell trapping and DNA damage analysis using microwell arrays," PNAS, Jun. 2010, 107(22):10008-10013.
Worthington et al., "Cloning of random oligonucleotides to create single-insert plasmid libraries," Anal Biochem, 2001, 294(2):169-175.
Wright et al., "Reusable, reversibly sealable parylene membranes for cell and protein patterning," J Biomed Mater Res A., May 2008, 85(2):530-538.
Xia et al., "Spatial transcriptome profiling by MERFISH reveals subcellular RNA compartmentalization and cell cycle-dependent gene expression," Proceedings of the National Academy of Sciences, Sep. 2019, 116(39):19490-19499.
Yamauchi et al., "Subcellular western blotting of single cells," Microsyst Nanoeng., 2017, 3:16079, 9 pages.
Yershov et al., "DNA analysis and diagnostics on oligonucleotide microchips," Proc. Natl. Acad. Sci. USA, May 1996, 93(10):4913-4918.
Yusof et al., "Inkjet-like printing of single-cells," Lab Chip, Jul. 2011, 11(14):2447-2454.

(56) References Cited

OTHER PUBLICATIONS

Zhang et al., "Block-Cell-Printing for live single-cell printing," PNAS, Feb. 2014, 111(8):2948-2953.

Zheng et al., "Massively parallel digital transcriptional profiling of single cells," Nat Commun., Jan. 16, 2017, 8:14049, 12 pages.

Zhu et al., "Reverse transcriptase template switching: a SMART approach for full-length cDNA library construction," Biotechniques, Apr. 2001, 30(4):892-897.

O'Huallachain et al., "Ultra-high throughput single-cell analysis of proteins and RNAs by split-pool synthesis," Communications Biology, 2020, 3:213, 19 pages.

Satija et al., "Spatial reconstruction of single-cell gene expression data," Nature, Apr. 13, 2015, 33(5):495-402, 14 pages.

Stoeckius et al., "Simultaneous epitope and transcriptome measurement in single cells," Nature Methods, Jul. 31, 2017, 14(9):865-868.

Adam et al., "Psychrophilic proteases dramatically reduce single-cell RNA-seq artifacts: a molecular atlas of kidney development," Development, Oct. 1, 2017, 144(19):3625-3632.

Eastburn et al., "Identification of Genetic Analysis of Cancer Cells with PCT-activated Cell Sorting," Nucleic Acids Research, Jul. 16, 2014, 42(16):e128, 10 pages.

Eastburn et al., "Ultrahigh-throughput Mammalian Single Cell Reverse-transcriptase Polymerase Chain Reaction in Microfluiding Drops," Analytical Chemistry, American Chemical Society, Aug. 20, 2013, 85(16):8016-8021.

Edsgard et al., "Identification of spatial expression trends in single-cell gene expression data," Nature Methods, Mar. 19, 2018, 15:339-342, 16 pages.

Ha et al, "Self-assembly hollow nanosphere for enzyme encapsulation," Soft Matter, Feb. 11, 2010, 6, 1405-1408, 10 pages.

Hu et al., "A thermo-degradable hydrogel with light-tunable degradation and drug release," Biomaterials, Jan. 2017, 112:133-140.

Ju et al, "Supramolecular dendrimer capsules by cooperative binding," Chem. Commun., Jan. 7, 2011, 47(1):268-270, 8 pages.

Kuiper et al, "Enzymes containing porous polymersomes as nano reaction vessels for cascade reactions," Org. Biomol, Chem, Oct. 15, 2008, 6(23):4315-4318.

Liu et al., "Preparation and Characterization of Temperature-Sensitive Poly(N-isopropylacrylamide)-b-poly(d,1-lactide) Microspheres for Protein Delivery," Biomacromolecules, 2003, 4(6):1784-1793.

Lyu et al., "One-Pot Synthesis of Protein-Embedded Metal-Organic Frameworks with Enhanced Biological Activities," Nano Lett., Sep. 11, 2014, 14:5761-5765.

Massoni-Badosa et al, "Sampling artifacts in single-cell genomics cohort studies," bioRxiv, Jan. 15, 2020, 32 pages.

Miller et al., "Rapid and Efficient Enzyme Encapsulation in a Dendrimer Silica Nanocomposite," Macromolecular Bioscience, Oct. 25, 2006, 6(10):839-845.

O'Flanagan et al, "Dissociation of solid tumor tissues with cold active protease for single-cell RNA-seq minimizes conserved collagenase-associated stress responses," Genome Biology, Oct. 17, 2019, 20:210, 13 pages.

Pellegrino et al, "High-throughput Single-cell DNA Sequencing of Acut Myeloid Leukemia Tumors with Droplet Microfluidics," Genome Research, Aug. 7, 2018, 28(9):1345-1352.

Rahimi et al, "Synthesis and Characterization of Thermo-Sensitive Nanoparticles for Drug Delivery Applications," J. Biomed. Nanotechnol. Dec. 2008, 4(4):482-490, 19 pages.

Shieh, et al., "Imparting Functionality to Biocatalysts via Embedding Enzymes into Nanoporous Materials by a de Novo Approach: Size-Selective Sheltering of Catalase in Metal—Organic Framework Microcrystals," J Am Chem Soc., Apr. 8, 2015, 137(13):4276-4279, 4 pages.

Soderberg, "Droplet Microfluidics Reverse Transcription and PCR Towards Single Cell and Exosome Analysis," Doctoral Thesis, KTH School of Biotechnology Science for Life Laboratory, 2017, 69 pages.

Sun et al., "Statistical Analysis of Spatial Expression Pattern for Spatially Resolved Transcriptomic Studies," Nature Methods, Jan. 27, 2020, 17(2): 193-200.

Svensson et al., "SpatialDE: identification of spatially variable genes," Nature Methods, May 2018, 15:343-346, 15 pages.

Luo et al., "Probing infectious disease by single-cell RNA sequencing: Progresses and perspectives," Computational and Structural Biotechnology Journal, Oct. 21, 2020, 18:2962-2971.

Marx, "Method of the Year: spatially resolved transcriptomics," Nature Methods, 2021, 18(1):9-14.

Vickovic et al., "Massive and parallel expression profiling using microarrayed single-cell sequencing," Nat. Commun. Oct. 14, 2016, 7:13182, 9 pages.

Seliff, I. et al., "High-Throughput Mapping of B Cell Receptor Sequences to Antigen Specificity", Cell, vol. 179, Issue 7, 2019, pp. 1636-1646.e15, ISSN 0092-8674, https://doi.org/10.1016/j.cell.2019.11.003.

Lu et al., "Highly multiplexed profiling of single-cell effector functions reveals deep functional heterogeneity in response to pathogenic ligands," PNAS, Feb. 2, 2015, E607-E615.

Lu et al., "Highly multiplexed profiling of single-cell effector functions reveals deep functional heterogeneity in response to pathogenic ligands," PNAS, Feb. 2, 2015, E607-E615 (Supplementary Information), 94 pages.

Asp et al., "A spatiotemporal organ-wide gene expression and cell atlas of the developing human heart," Cell, Dec. 12, 2019, 179(7):1647-1660.

Fiskin et al., "Single-cell multimodal profiling of proteins and chromatin accessibility using PHAGE-ATAC," bioRxiv, posted Oct. 20, 2020, 63 pages.

Kuhn et al., "A novel, high-performance random array platform for quantitative gene expression profiling," Genome Res, 2004, 14:2347-2356.

10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

Gerard et al., "High-throughput single-cell activity-based screening and sequencing of antibodies using droplet microfluidics," Nature Biotechnology, Jun. 2020, 38(6):715-721, 19 pages.

Hatori et al., "Particle-Templated Emulsification for Microfluidics-Free Digital Biology," Anal. Chem., 2018, 90:9813-9820.

\* cited by examiner

SYSTEMS AND METHODS FOR DETECTING ANALYTES FROM CAPTURED SINGLE BIOLOGICAL PARTICLES

CROSS-REFERENCE TO RELATED APPLICATIONS

This application claims priority or the benefit of U.S. Provisional Patent Application 63/033,348 filed Jun. 2, 2020, the contents of which are fully incorporated herein by reference.

BACKGROUND

Detection and quantification of analytes in single biological particles (e.g., single cells or nuclei), can answer questions not easily answered by methods that measure average levels of specific analytes in populations of biological particles. Single-biological particle detection and quantification of analytes and their expression is currently an active area of research and development. New systems and methods for single-biological particle (e.g., single cell or nucleus) analyte measurement are of interest.

SUMMARY

Disclosed here are systems and methods for selecting and retaining single biological particles (e.g., single cells or nuclei) based on their binding to specific substances located on a substrate. Detection and analysis of specific analytes from the single biological particles (e.g., single cells or nuclei) provides for detection and identification of analytes from the bound biological particles that are related or specific to the biological particle-binding event and/or substances or molecules responsible for the biological particle binding.

Disclosed here are systems that may include a substrate, a biological particle (e.g., cell or nucleus) capture moiety attached to the substrate and a plurality of barcode molecules associated with the biological particle (e.g., cell or nucleus) capture moiety. The barcode molecules may include a common barcode sequence and an analyte binding sequence. The substrate may have multiple capture moieties for biological particles, each biological particle capture moiety having barcode molecules with a different common barcode sequence. The multiple biological particle capture moieties may be arranged on the substrate such that, when used in the methods disclosed herein, diffusion of an analyte from the biological particles is limited to the barcode molecules associated with the biological particle capture moiety that bound the biological particle. Diffusion of analytes from one biological particle capture moiety to another or to adjacent biological particle capture moieties is prevented or minimized. The biological particle capture moieties may contain a substance to which a biological particle (e.g., cell or nucleus) may bind. The binding may be specific in that, in some examples, biological particles may have a receptor that binds to a ligand that is part of the biological particle binding moiety. The biological particle receptors may bind to specific ligands. Biological particles not having receptors for a specific ligand may not bind to the substrate. Ligands may be proteins, polypeptides, peptides, polysaccharides, saccharides, sugars, lipids, nucleic acids, and the like.

In some instances, ligands to which cells of the immune system may specifically bind are used as part of biological particle (e.g., cell or nucleus) capture moieties. Peptide epitopes to which specific TCRs of T-cell lymphocytes or to which specific BCRs of B-cell lymphocytes may bind may be used in these cell capture moieties. In some instances, more than one substance or molecule may be part of biological particle capture moieties. For example, a biological particle capture moiety having a peptide molecule may also include an MHC-I and/or MHC-II molecule. The MHC molecules may be part of MHC multimers. The barcode molecules may include analyte binding sequences designed to capture different types of analytes. In some instances, a barcode molecule may be configured to bind a single analyte. In some instances, the analyte binding sequences may be nucleotide sequences capable of hybridizing to analytes from the biological particles (e.g., RNAs) having complementary nucleotide sequences, or capable of hybridizing to complements or amplification products of analytes from biological particles. In some instances, the analyte binding sequences of the barcode molecules may have nucleotide sequences able to hybridize with cellular RNAs, or complements or amplification products thereof, that encode rearranged V(D)J sequences of a T-cell receptor (TCR) or a B-cell receptor (BCR).

Also disclosed are systems that may include a substrate and a plurality of biological particle (e.g., cell or nucleus) capture regions. The biological particle capture regions may include a biological particle capture moiety and a plurality of barcode molecules. The barcode molecules may include a common barcode sequence and an analyte binding sequence. The substrate may have between about 1,000 biological particle capture regions and 100 million biological particle capture regions. A biological particle capture region may be between about 10 and 1,000 microns from one edge to another. A distance between adjacent biological particle capture regions may be between about 1 and 100 microns. A biological particle capture region may have between about 1,000 barcode molecules and 1 billion barcode molecules.

Methods for making the disclosed systems are disclosed. In some examples of these methods, molecules intended to be part of biological particle capture moieties may be printed to the substrate of the disclosed systems. In some examples of these methods, barcode molecules intended to be part of the system may be printed to a substrate of the disclosed systems.

Disclosed here also are methods whereby the disclosed systems may be used to capture single biological particles and examine analytes from the biological particles on a single-biological particle (e.g., cell or nucleus) basis. In some instances, a population of cells or nuclei may be placed in contact with the biological particle capture moieties of the system and a subset of cells or nuclei from the population that binds the biological particle capture moieties may be retained on the substrate. In some instances, cells or nuclei that do not specifically bind the biological particle capture moieties may be washed away. This may include cells or nuclei with no or with low binding affinity for substances of the biological particle capture moieties. Various methods may be used to select, retain or remove cells or nuclei that have certain binding affinities for the biological particle capture moieties.

In some instances, biological particle capture moieties may be used to select and retain T-cells having TCRs, or B-cells having BCRs, that bind peptides having specific amino acid sequences. The peptides may be part of biological particle capture moieties in the context of MHC molecules. In some instances, the MHC molecules may be part of MHC multimers. Analytes from cells or nuclei retained on the substrate may be released from the retained cells or nuclei, for example by permeabilizing the cells or nuclei, such that analytes from the retained cells or nuclei contact barcode molecules adjacent to or associated with the biological particle capture moieties that bound the cells or nuclei. Barcode molecules with analyte binding sequences capable of binding specific analytes will bind/capture those analytes. In some instances, the plurality of barcode molecules associated with individual cell or nucleus binding moieties may contain analyte binding sequences specific for many or all analytes from a cell or nucleus. In these cases, the analyte composition of specific retained cells or nuclei may be detected and/or analyzed through analysis of the barcode molecules that have bound an analyte. In some instances, the plurality of barcode molecules associated with the biological particle binding moieties may contain analyte binding sequences specific for less than all analytes from a cell or nucleus. Barcode molecules with analyte binding sequences for a few or for rare analytes may be used. In some instances, barcode molecules containing analyte binding sequences capable of binding cellular or nuclear analytes (e.g., mRNAs) containing rearranged V(D)J sequences may be used. In the case where T-cells were retained on a substrate based on affinity of their TCRs for a peptide epitope of known amino acid sequence, identification of analytes from the bound cells that have specific rearranged V(D)J sequences determines the pairing of the peptide epitope with its cognate TCR. A similar determination can be made for peptides specific for BCRs of a B-cell.

In some examples of the disclosed methods, after biological particle (e.g., cell or nucleus) retention on the substrate, and cell/nucleus release of analytes, and their binding to barcode molecules having specific analyte binding sequences, the barcode molecules are used as templates in amplification reactions to generate molecules comprising the barcodes common to individual biological particle capture moieties, barcodes common to the same or related bound analytes, and/or barcodes specific to individual barcode molecules. The nucleotide sequences of these molecules maybe be obtained through DNA sequencing. Analysis of the nucleotide sequences, in relation to the substances/molecules in specific cell binding moieties that bind cells from which the analytes are obtained, reveals the relationships between biological particle (e.g., cell or nucleus) binding and specific analytes from the biological particle.

INCORPORATION BY REFERENCE

The following U.S. patents and U.S. published patent applications are each incorporated by reference in their entirety into this application:

U.S. Pat. No. 10,550,429 (Ser. No. 16/426,762), issued Feb. 4, 2020 and titled, "Methods And Systems For Processing Polynucleotides";

U.S. Provisional Patent Application Ser. No. 62/982,495, filed Feb. 27, 2020 and titled "Solid State Single Cell Method For Analyzing Fixed Biological Cells";

U.S. Pat. No. 10,030,261 (Ser. No. 14/111,482), issued Jul. 24, 2018 and titled, "Method And Product For Localized Or Spatial Detection Of Nucleic Acid In A Tissue Sample";

U.S. Pat. No. 9,593,365 (Ser. No. 14/434,274), issued Mar. 14, 2017 and titled, "Methods And Product For Optimising Localized Or Spatial Detection Of Gene expression In A Tissue Sample"; and U.S. Patent Publication No. 10,774,374 (Ser. No. 15/565,637), issued Sep. 15, 2020 and titled, "Spatially Distinguished, Multiplex Nucleic Acid Analysis of Biological Specimens".

Other references incorporated by reference may be listed throughout the application.

BRIEF DESCRIPTION OF THE DRAWINGS

In the accompanying drawings, which are incorporated in and constitute a part of the specification, embodiments of the disclosed inventions are illustrated. It will be appreciated that the embodiments illustrated in the drawings are shown for purposes of illustration and not for limitation. It will be appreciated that changes, modifications and deviations from the embodiments illustrated in the drawings may be made without departing from the spirit and scope of the invention, as disclosed below.

The TCRs, and thus the T-cell lymphocytes, that have bound to the top biological particle capture region are different than the TCRs and T-cell lymphocytes that have bound to the bottom biological particle capture region.

Figure 9:
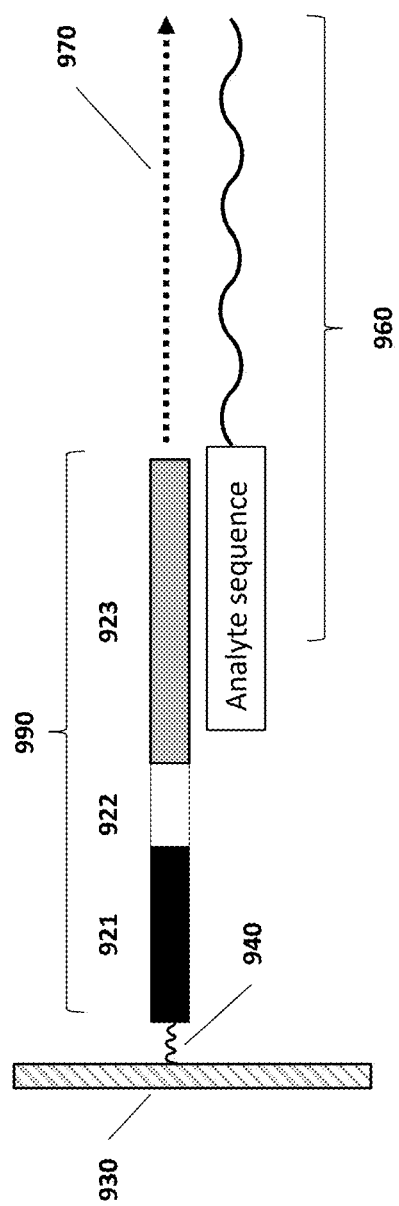

FIG. 9 is a schematic drawing (side view) that illustrates an example of a barcode molecule of this disclosure.

Figure 10A:
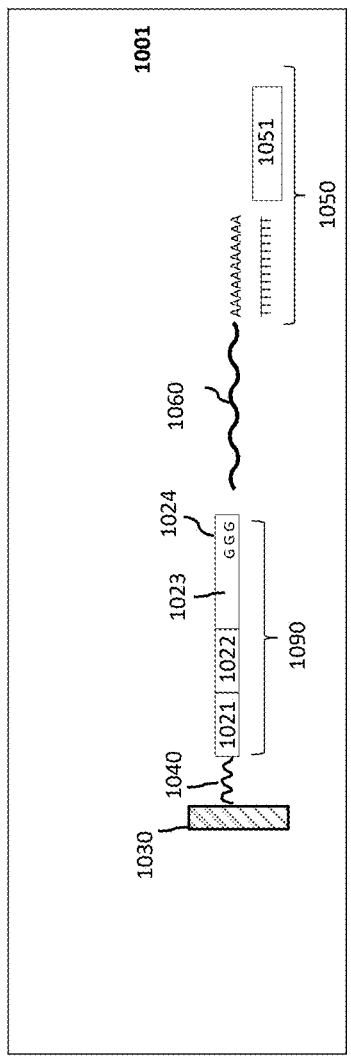
Figure 10B:
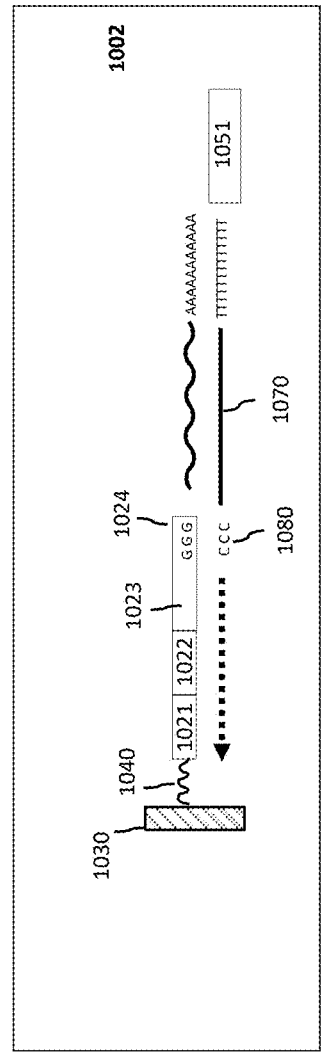

FIGS. 10A and 10B are schematic drawings illustrating an example of reverse transcription of cDNA including addition of non-templated bases.

DETAILED DESCRIPTION

The systems and methods described here are for capturing biological particles (e.g., cells or nuclei), generally single biological particles. Capturing the biological particles is based on their binding to specific substances located on a substrate. Analytes from the biological particles are captured, and the captured analytes are analyzed, generally to provide information on presence and/or amounts of specific analytes within the captured biological particles.

In some examples, immune cells and can be used for processing of single analytes (e.g., RNA, DNA, or protein) or multiple analytes simultaneously (e.g., DNA and RNA, DNA and protein, RNA and protein, or RNA, DNA and protein) (see WO 2019/157529A1 (Appl. No. PCT/US2019/017723), which is incorporated herein by reference in its entirety). In one embodiment, the analytes are intracellular analytes (e.g., nucleic acids such as mRNA and intracellular proteomic analytes such as peptides and polypeptides). The analytes may also be analytes expressed on the extracellular surface of a biological particle (e.g., an extracellular polypeptide or other molecule) (see U.S. Pat. Publ. No. 2020/0002763; Ser. No. 16/439,675; see WO 2019/157529A1; Appl. No. PCT/US2019/017723; both of which are incorporated herein by reference in their entirety).

Definitions

Herein, "affinity" refers to attraction between objects. In some examples, affinity refers to the strength of a binding interaction between biological particles, like cells, nuclei or individual molecules (e.g., receptor and ligand).

Herein, "amplification product" refers to molecules that result from reproduction or copying of a molecule. Generally, the molecules copied or reproduced are nucleic acid molecules, specifically DNA or RNA molecules. In some examples, the molecule reproduced or copied may be used as a template for the produced molecules. Generally, the reproduction that occurs to produce amplification products uses enzymatic reactions. Examples of enzymes that may result in amplification products include polymerases, transcriptases, and the like. Reverse transcriptases and Taq polymerases are specific examples of these enzymes.

Herein, "analyte" refers to a substance whose chemical constituents are being identified and/or measured. Generally, this application refers to analytes from and/or produced by biological particles (e.g., cells and/or nuclei). Any or all molecules or substance from or produced by a biological particle may be referred to herein as analytes. Chemically, cellular analytes may include proteins, polypeptides, peptides, saccharides, polysaccharides, lipids, nucleic acids, and other biomolecules.

Herein, "analyte binding sequence" refers to a part of a barcode molecule that is capable of binding or capturing an analyte. An analyte binding sequence may be capable of capturing analytes that may include proteins, polypeptides, peptides, saccharides, polysaccharides, lipids, nucleic acids, and other biomolecules. In some examples, the analyte binding sequence is a nucleotide sequence capable of hybridizing to an analyte that contains a complementary nucleotide sequence.

Herein, "antibody" generally refers to all types of antibodies, fragments and/or derivatives. Antibodies include polyclonal and monoclonal antibodies of any suitable isotype or isotype subclass. Herein, antibody may refer to, but not be limited to Fab, F(ab')$_2$, Fab' single chain antibody, Fv, single chain, mono-specific antibody, bi-specific antibody, tri-specific antibody, multi-valent antibody, chimeric antibody, canine-human chimeric antibody, chimeric antibody, humanized antibody, human antibody, CDR-grafted antibody, shark antibody, nanobody (e.g., antibody consisting of a single monomeric variable domain), camelid antibody (e.g., from the Camelidae family) microbody, intrabody (e.g., intracellular antibody), and/or de-fucosylated antibody and/or derivative thereof. Mimetics of antibodies are also provided.

Herein, "antigen" refers to substances that induce immune responses in the body. Peptides are one example of a type of antigen.

Herein, "array" refers to a region on a support that contains multiple demarcated regions of oligonucleotides, interspersed with intervening regions that do not contain oligonucleotides. In some examples, these regions may be referred to as "oligonucleotide arrays" or "capture areas". The arrays herein generally have oligonucleotides that contain spatial barcodes and, thus, the arrays may be referred to as "spatial" arrays.

Herein, "associated with" generally refers to barcode molecules that are in close proximity to a particular biological particle (e.g., cell or nucleus) capture moiety on a substrate. Generally, herein, barcode molecules associated with a particular biological particle capture moiety are distributed around that capture moiety such that analytes released from a biological particle (e.g., cell or nucleus) captured by or bound to that biological particle capture moiety will contact the barcode molecules associated with that biological particle capture moiety and will not contact barcode molecules associated with other or adjacent biological particle capture moieties. Herein, analytes released from biological particles or nuclei bound to cell capture moieties, for example, generally reach the associated barcode molecules by diffusion. A released analyte will have a better probability of contacting a barcode molecule, the closer the barcode molecule is located to the biological particle capture moiety which bound the biological particle.

Herein, "attached to" refers to the relationship of barcode molecules to a substrate. Barcode molecules attached to the substrate are stationary or immobilized on the substrate. Herein, one end of a barcode molecule is generally chemically linked to the substrate. Herein, barcode molecules attached to a substrate are capable of binding analytes and being used as templates for amplification reactions, for example.

Herein, "B-cell lymphocyte" refers to a type of cell (a biological particle) from the immune system. B-cell lymphocytes are a type of white blood cell that functions in the humoral immunity component of the adaptive immune response. In some examples, B-cell lymphocytes secrete or are capable of secreting antibodies. In some examples, B-cell lymphocytes have B-cell receptors (BCR) on their surfaces.

Herein, "B-cell receptor" or "BCR" refers to a transmembrane receptor protein or proteins on the surface of B-cell lymphocytes. BCRs generally control the activation of B-cell lymphocytes. BCRs are capable of binding specific antigens, including specific peptide epitopes of antigens.

Herein, "barcode," generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

Herein, "barcoded molecule" or, in some examples, "barcoded nucleic acid molecule" generally refers to a molecule or a nucleic acid molecule that results from, for example, the processing of a nucleic acid barcode molecule with a nucleic acid sequence (e.g., nucleic acid sequence complementary to a nucleic acid primer sequence encompassed by the nucleic acid barcode molecule). The nucleic acid sequence may be a targeted sequence (e.g., targeted by a primer sequence) or a non-targeted sequence. For example, in the methods, systems and kits described herein, hybridization and reverse transcription of the nucleic acid molecule (e.g., a messenger RNA (mRNA) molecule) of a cell with a nucleic acid barcode molecule (e.g., a nucleic acid barcode molecule containing a barcode sequence and a nucleic acid primer sequence complementary to a nucleic acid sequence of the mRNA molecule) results in a barcoded nucleic acid molecule that has a sequence corresponding to the nucleic acid sequence of the mRNA and the barcode sequence (or a reverse complement thereof). A barcoded nucleic acid molecule may be a nucleic acid product. A barcoded nucleic acid molecule may serve as a template, such as a template polynucleotide, that can be further processed (e.g., amplified) and sequenced to obtain the target nucleic acid sequence. For example, in the methods and systems described herein, a barcoded nucleic acid molecule may be further processed (e.g., amplified) and sequenced to obtain the nucleic acid sequence of the mRNA.

Herein, molecules stated to have a "common barcode sequence" refers to molecules that are labeled or identified with the same barcode sequence.

Herein, "bind" generally refers to a stable physical interaction between substances. Biological particles (e.g., cells or nuclei) may bind to other biological particles. Biological particles may bind to molecules. Molecules may bind to biological particles. Molecules may bind to other molecules. In some examples, binding of substances may be specific. Example specific binding events include cell-receptor binding of a ligand and antibody binding of an antigen. In some examples, two substances that specifically bind to one another may have a higher affinity for each other than two substances that nonspecifically bind to each other or which do not bind to each other. Under certain conditions, specific binding of substances may occur, while non-specific binding of substances may not occur. "Binding" refers to causing substances to bind.

The term "biological particle," as used herein, generally refers to a discrete biological system derived from a biological sample. The biological particle may be a macromolecule, small molecule, virus, cell, cell derivative, cell nucleus, cell organelle, cell constituent and the like. Examples of a cell organelle include, without limitation, a nucleus, endoplasmic reticulum, a ribosome, a Golgi apparatus, an endoplasmic reticulum, a chloroplast, an endocytic vesicle, an exocytic vesicle, a vacuole, and a lysosome. The biological particle may contain multiple individual components, such as macromolecules, small molecules, viruses, cells, cell derivatives, cell nuclei, cell organelles and cell constituents, including combinations of different of these and other components. The biological particle may be or may include DNA, RNA, organelles, proteins, or any combination thereof. These components may be extracellular. In some examples, the biological particle may be referred to as a clump or aggregate of combinations of components. In some instances, the biological particle may include one or more constituents of a cell but may not include other constituents of the cell. An example of such constituents include nucleus or an organelle. A cell may be a live or viable cell. The live cell may be capable of being cultured, for example, being cultured when enclosed in a gel or polymer matrix or cultured when comprising a gel or polymer matrix.

Herein, "capture" generally refers to the capability of a first substance to interact with and/or bind a second substance, where the second substance is part of a population of other substances. In some examples, a plurality of biological particle capture moieties may "capture" a subpopulation of biological particles (e.g., cells or nuclei) from a biological particle population. Herein, for example, a cell or nucleus may be captured. An analyte may be captured. In some examples, capture refers to identification of a target nucleic acid molecule (e.g., an RNA) by hybridization using a nucleic acid probe for the target nucleic acid molecule, and/or amplification of a target nucleic acid molecule or a nucleic acid probe hybridized to it (e.g., an RNA or a probe hybridized to the RNA) using, for example polymerase chain reactions (PCR) and/or nucleic acid extension of a target nucleic acid molecule or a nucleic acid probe hybridized to it (e.g., an RNA or a probe hybridized to the RNA) using, for example reverse transcription reactions. Capturing refers to causing a first substance to capture a second substance.

Herein, "biological capture moiety" (e.g., cell-capture moiety or nucleus-capture moiety) refers to a location on a substrate to which a biological particle may bind. Generally, a biological particle capture moiety may have or contain substances to which a biological particle may bind. The biological particle binding to the substances may be specific binding. In some examples, the substances may be molecules to which certain biological particles may specifically bind. In some examples, the substances may be specific ligands or cognate ligands for receptors on a biological particle.

Herein, "biological particle capture region" refers to a region on a substrate that contains a capture moiety for a biological particle and a plurality of barcode molecules associated with the capture moiety. A "cell capture region" refers to a region on a substrate that contains a cell capture moiety and a plurality of barcode molecules associated with the cell capture moiety. A "nucleus capture region" refers to a region on a substrate that contains a nucleus capture moiety and a plurality of barcode molecules associated with the nucleus capture moiety.

Herein, "cells from the immune system" generally refers to groups of cells categorized as lymphocytes (e.g., T-cells, B-cells, NK cells), neutrophils, and monocytes/macrophages. These are types of white blood cells.

Herein, "complementary," in the context of one sequence of nucleic acids being complementary to another sequence, refers to the ability of two strands of single-stranded nucleic acids to form hydrogen bonds between the two strands, along their length. A complementary strand of nucleic acids is generally made using another nucleic acid strand as a template.

Herein, "configured to" generally refers to a component of a system that can perform a certain function.

Herein, "contact" refers to physical touching of separate substances. "Contacting" refers to causing separate substances to physically touch one another.

Herein, "correlate" means that one thing affects or depends on another thing. "Correlating" refers to identification of the separate things that affect or depend on one another and, in some examples, refers to quantifying the relationship between the separate things.

Herein, "diffusion" means to spread over an area. Generally, herein, analytes diffuse from a biological particle to contact barcode molecules associated with a biological particle capture moiety that is part of the capture region to which the biological particle has bound.

Herein, "epitope" refers to parts of an antigen that bind to or are bound by, for example, a T-cell receptor, B-cell receptor or antibody.

Herein, "fix," refers to formation of covalent bonds, such as crosslinks, between biomolecules or within molecules. The process of fixing, cells for example, is called "fixation." The agent that causes fixation is generally referred to as a "fixative" or "fixing agent." "Fixed cells" or "fixed tissues" refers to cells or tissues that have been in contact with a fixative under conditions sufficient to allow or result in formation of intra- and inter-molecular covalent crosslinks between biomolecules in the biological sample. Fixation may be reversed and the process of reversing fixation may be referred to, for example, as "decrosslinking." Cells that are not fixed may be referred to as fresh or unfixed cells.

Herein, "flow" refers to a moving liquid. "Flowing" refers to causing a liquid to flow. Generally, herein, flowing refers to causing a liquid containing biological particles to contact biological particle capture moieties.

Herein, "generate" means to make or produce. Generally, herein, generate is used to describe producing molecules (e.g., making an amplification product) using barcode molecules as templates.

Herein, "hybridize" refers to a nucleotide sequence of a single-stranded nucleic acid molecule forming a complex with a nucleic acid molecule having a complementary nucleotide sequence. Generally, the complex forms through hydrogen bonding between complementary nucleotide bases in separate nucleic acid molecules.

Herein, "hybridizing nucleotide sequence" refers to a nucleotide sequence, within an oligonucleotide for example, that is capable of hybridizing with a complementary nucleotide sequence in a target nucleic acid molecule present on or within a cell from a tissue sample (e.g., cellular RNA). When a hybridizing nucleotide sequence is of such a length that it hybridizes with a complementary nucleotide sequence that is unique to a target nucleic acid molecule(s) (e.g., cellular RNA or family of RNAs), the hybridizing nucleotide sequence may be said to hybridize to the same target nucleic acid molecule (e.g., the same RNA).

Herein, "identity," may be used to refer to a peptide that is part of a biological particle capture moiety or to a biological particle capture moiety itself. Generally, it is the "identity" of the peptide or biological particle capture moiety that is related to the type of biological particle bound to the biological particle capture moiety (e.g., T-cell lymphocyte), and which is correlated with analytes captured by analyte binding sequences that are associated with the biological particle capture moiety to which the biological particle has bound.

Herein, "immobilize" means to restrict or prevent movement.

Herein, "intervening region" or "interspot space" refers to areas on a support or
substrate that do not contain attached oligonucleotides.

Herein, "labeling agent" refers to molecules, substances and the like, that can be used to label or tag biological particles (e.g., cells or nuclei), and can be bound by biological particle capture moieties to retain biological particles on a support.

Herein, "library" refers to a collection of molecules having nucleotide sequences that are generally representative (e.g., comprising the same nucleotide sequences or complementary nucleotide sequences) of nucleotide sequences present in the molecules from the target nucleic acids. Generally, the molecules from which a library is made act as templates for synthesis of the collection of molecules that make up the library. The "library" may be, or may be produced from, amplification products of the target nucleic acid. Herein, libraries can be created from amplification of a mRNA analyte, or copies thereof, captured on an array. Therefore, the library can be derived from the captured target nucleic acid.

Herein, "ligand" refers to a molecule to which a receptor binds. In some examples, receptor binding of a ligand is specific binding.

Herein, "major histocompatibility complex" or "MHC" refers to genetic loci in vertebrate genomes that contain related polymorphic genes that encode cell surface proteins essential for the adaptive immune system. MHC molecules refer to RNAs and/or proteins encoded by the genetic locus.

Herein, "major histocompatibility class I molecule" or "MHC-I molecule" refers to a group of MHC molecules, generally expressed in nucleated cells and platelets, that are responsible for presenting epitopes to T-cell lymphocytes. MHC-I molecules generally mediate cellular immunity.

Herein, "major histocompatibility class II molecule" or "MHC-II molecule" refers to MHC molecules, generally expressed on macrophages, B-cell lymphocytes and dendritic cells, that are responsible for presenting epitopes to T-cell lymphocytes. MHC-II molecules generally mediate humoral immunity.

Herein, "MHC matched" (or HLA match, which is specific to humans) refers to a close relationship between MHC molecules. In the context of this application, the MHC molecules of a T-cell may need to be closely related or "matched" to MHC molecules of a cell capture moiety, if the TCRs of the T-cell are to specifically bind a peptide epitope that is also part of the cell capture moiety.

Herein, "MHC multimer" refers to oligomeric forms of MHC molecules. An example MHC multimer is an MHC dextramer.

Herein, a "nucleic acid product" refers to a nucleic acid produced using a target nucleic acid molecule (e.g., an RNA) as a template, and derivatives thereof. In some examples, a nucleic acid probe (e.g., an RNA capturing probe) may act as a primer for a nucleic acid extension reaction (e.g., a reverse transcription reaction or a polymerase chain reaction) that extends (or amplifies) a nucleotide sequence of the target nucleic acid molecule, thus generating nucleic acid products based on the target nucleic acid molecule or the nucleic acid probe.

Herein, "nucleotide capture sequence" refers to an analyte binding sequence that can capture a nucleic acid molecule, generally having a specific nucleotide sequence.

Herein, "nucleotide sequence" refers to a linear progression of nucleotide bases within a nucleic acid molecule (e.g., oligonucleotide).

Herein, "oligonucleotide" means a linear polymer of nucleotides, in some examples 2'-deoxyribonucleotides. Oligonucleotides are single stranded. Oligonucleotides can be of various lengths. Oligonucleotides can include modified nucleotides as known in the art.

Herein, "obtain" means to acquire. "Obtaining" is an act performed to obtain something.

Herein, "partition" generally, refers to a space or volume that may be suitable to contain one or more species or conduct one or more reactions or processes. A partition may be a physical compartment, such as a droplet or well (e.g., a microwell). The partition may isolate space or volume from another space or volume, such as regions between capture regions on an array where there are typically no capture oligonucleotides. Herein, regions on an array where there are typically no capture oligonucleotides may also be referred to as intervening regions.

Herein, "peptide" refers to two or more amino acids covalently joined by peptide bonds. In some examples, a peptide may contain no more than 30, 40, 50 or 100 amino acids. A peptide specifically recognized by immune cells, such as by a TCR of a T-cell lymphocyte, may be referred to as a peptide "epitope."

Herein, "permeable" refers to the state of a biological particle such that analytes can flow out of the biological particle. "Permeabilize" refers to causing biological particles (e.g., cells or nuclei) to be permeable. In some examples, permeabilization of cells involves affecting the structure of cell membranes such that analytes can diffuse out from the cells. In some examples, mild detergents may be used to permeabilize cells.

Herein, "planar" refers to the shape of a plane (e.g., flat).

Herein, "plurality" means multiple.

Herein, "population," when referring to biological particles, means a large number of biological particles. Biological particles that make up a population may be similar or may be dissimilar. A group of biological particles from a population, that contains fewer biological particles than the complete population, may be referred to as a subpopulation.

Herein, "primer" means a single-stranded nucleic acid sequence that provides a starting point for DNA synthesis. Generally, a primer has a nucleotide sequence that is complementary to a template and has an available 3'-hydroxyl group to which a transcriptase or polymerase can add additional nucleotides complementary to corresponding nucleotides in the template, to synthesize a nucleic acid strand in 3' to 5' direction.

Herein, "print" means to apply something to a substrate or surface in a particular way or to a particular location. Printing refers to the act of applying something to a substrate.

Herein, "provide" means to make available. Providing is the act of making something available.

Herein, "rearranged V(D)J" refers to a particular arrangement of specific genes in T-cells and B-cells, that arises from genome rearrangement of particular V, D and J gene segments in germline cells. The rearrangement process involves somatic recombination and is responsible for the diverse repertoire of antibodies (B-cells) and T-cell receptors (T-cells) found in vertebrate organisms. The rearrangement generally occurs during lymphocyte development. Generally, a single mature B-cell or T-cell will have a single rearranged configuration of V(D)J gene segments related to heavy and light chains of B-cell receptors and to alpha- and beta-subunits of T-cell receptors.

Herein, "receptor" refers to a molecule that binds a ligand. In some examples, receptor binding of a ligand is specific binding.

Herein, "release" generally refers to a biological particle which is bound to a biological particle capture moiety, no longer being bound by the capture moiety. Releasing is the process of a bound biological particle becoming unbound from a capture moiety.

Herein, "retain" generally refers to a biological particle bound to a biological particle capture moiety and being immobilized there. "Retaining in place" may refer to this state of a biological particle on a substrate.

Herein, "RNA capturing probe" refers to a nucleic acid molecule capable of hybridizing to an RNA.

Herein, "RNA-derived amplification product" refers to a nucleic acid produced using an RNA as template, and derivatives thereof. In some examples, an RNA capturing probe may act as a primer for a reverse transcriptase and/or polymerase chain reaction that amplifies a nucleotide sequence of the RNA, thus producing amplification products derived from the RNA.

Herein, "select" generally refers to obtaining specific biological particles from a population of biological particles. In some examples, subpopulations of biological particles may be obtained or selected from a biological particle population.

Herein, "spatial" refers to a location within or on a space. In some examples, the space may be a two-dimensional space.

Herein, "substrate" or "support" generally refers to a layer to which a substance may be applied and/or attached. A substrate/support may refer to something that serves, for example, as a foundation for another thing. In some examples, the support may be larger, more easily worked with, or more easily tracked or visualized than the thing being supported. A support may be a solid support. In some instances, a support may be dissolvable, disruptable, and/or degradable. In some cases, a support may not be degradable. A support may comprise a glass, plastic, metal, and/or other substances. In some cases, the support can be rigid. In other cases, the support may be flexible and/or compressible.

Herein, "surface" means the outside part or upper layer of something. Herein, a "surface" of an array generally refers to a surface of a support or substrate that has oligonucleotides attached.

Herein, "T-cell lymphocyte" refers to a type of cell (a biological particle) from the immune system. T-cell lymphocytes are a type of white blood cell that may function in the cellular component of the adaptive immune response, although some T-cells may play a role in humoral immunity. In some examples, T-cell lymphocytes have T-cell receptors (TCR) on their surfaces.

Herein, "T-cell receptor" or "TCR" refers to a receptor protein or receptor proteins on the surface of T-cell lymphocytes. Specific TCRs recognize and bind peptide antigens (e.g., epitopes), generally in the context of MHC molecules, and are responsible for regulating T-cell activation. Multiple different TCRs may recognize a given peptide epitope. TCRs are generally made up of TCRα and TCRβ subunits.

Herein, "template" refers to one single-stranded nucleic acid acting as a "template" for synthesis of another complementary single-stranded nucleic acid. For example, RNA can act as a template for synthesis of a complementary DNA strand synthesized using reverse transcriptase. A single-stranded DNA can act as a template for synthesis of a complementary DNA strand, most often by a DNA polymerase.

Herein, "unique molecular identifier" or "UMI" generally refers to an identifier of a particular analyte captured by a capture probe.

Biological Particles, Cells, Nuclei

The methods disclosed here are generally applicable to processing biological particles with a catalyst on a support and removing the support and attached catalyst to leave processed biological particles. In some examples, biological particles may be cells, parts of cells or cell organelles, like a cell nucleus. Cells may be of any kind or type. A cell may be a mammalian cell. A cell may be a eukaryotic cell or a prokaryotic cell. A cell may be an animal cell. A cell may be a human cell. A cell may be from a cell culture. A cell may be from an immortalized cell line. A cell may be from a primary sample, such as a patient sample. A cell may be from a frozen stock of cells (e.g., cryopreserved cells). The cells may be adherent cells or suspension cells. An adherent cell may be adhered to a surface. Alternatively, an adherent cell may be treated (e.g., with a chemical or biological reagent) to be separated from the surface, and thereby may be suspended in a sample.

Examples of cells may comprise a plant cell, animal cell, human cell, insect-derived cells, bacteria, algae, cardiomyocytes, stem cells, neurons, primary neurons, ESCs, iPSCs, hepatocytes, primary heart valve cells, primary hematopoietic cells, gastrointestinal cells, lymphocytes, T-cells, B-cells, natural killer cells, dendritic cells, hematopoietic cells, mononuclear phagocytes, granulocytes, beta cells, somatic cells, germ cells, embryos (human and animal), zygotes, gametes, and other types of cells. In some examples, a cell may be a therapeutic cell. For example, the cell may be suspected of having a therapeutic effect. The cell may be a stem cell. Example T-cell lymphocytes may include CD4+ T-cell lymphocytes or CD8+ T-cell lymphocytes.

In some instances, a cell may be a cancer cell. A cell may be from an immortalized cancer cell line. A cell may be a HeLa cell. A cell may be a breast cancer cell, a multiple myeloma cell, a lymphoma cell, or any other kind of cell. In some examples, different kinds of cells may be co-cultured and/or otherwise combined.

In some examples, the cells may be peripheral blood mononuclear cells or PBMCs. PBMCs may be isolated from whole blood. In some examples, PBMCs are isolated by taking whole blood, diluting the whole blood with a buffer (e.g., PBS), and layering the diluted whole blood over Ficoll or Ficoll-Paque in a tube that can be centrifuged. Centrifuging the layered tube (e.g., for 30-40 min at 400-500 g) results in four layers in the tube. The top layer is plasma and can be removed by pipetting. The second layer contains PBMCs. The second layer is generally white and cloudy. This layer can be removed with a pipette and added to warm PBS or medium to wash away any remaining platelets. The cells can be gently centrifuged into a pellet and viability of the cells estimated using Trypan blue staining. The cells can be used immediately or frozen for storage (i.e. cryopreserved). Other methods for isolating PBMCs from whole blood are known in the art.

In some examples, the biological particles (e.g., cells or nuclei) may be cryopreserved. In some examples, the biological particles (e.g., cells or nuclei) may be fresh or unfixed. In some examples, the biological particles (e.g., cells or nuclei) may be fixed.

Systems

Example systems of this application generally have at least three components: a substrate, a biological particle (e.g., cell or nucleus) capture moiety attached to the substrate and a plurality of barcode molecules associated with the biological particle capture moiety. In some examples, a biological particle capture moiety and the plurality of barcode molecules associated with it may be called a biological particle capture region. Generally, the substrates of this application contain multiple biological particle capture regions.

The single biological particles (e.g., cells or nuclei) can be captured on a surface or substrate having a plurality of barcoded spots or cell capture regions. Each biological particle capture region has an individual biological particle capture site or biological particle capture moiety that is designed for capture of one biological particle. The biological particle capture regions also have barcoded oligonucleotides that contain capture domains that bind analytes. The biological particle capture regions can be positioned at spaced intervals on any surface that is suitable for molecular barcoding and/or imaging and can be positioned at spaced intervals on a suitably primed surface of a substrate (e.g., a slide configured for reverse transcription of mRNA) used for molecular barcoding and/or imaging in spatial analysis. Various examples of the systems of this disclosure and their components are set forth in the following paragraphs and referenced figures.

In some examples, the substrate may be planar or substantially planar. In some examples, the shape of the substrate may be similar to that of a microscope slide or cover slip. Example substrates may flat and may lack microwells. Generally, the substrate is solid and example substrates may be glass or plastic. In some examples, the substrate is transparent to light. The substrates may be of various sizes and thicknesses. Dimensions of the substrates may be dictated by any instruments used to perform the methods disclosed in the application. The substrates may be configured to accept or attach biological particle (e.g., cell or nucleus) capture moieties and/or components thereof. The substrates may be configured to accept or attach barcode molecules. In some examples, the substrates and/or surfaces thereof, may be coated or modified to accept the biological particle capture moieties and/or barcode molecules. In some examples, biological particle capture moieties and/or barcode molecules may be printed onto a substrate.

Various examples of the systems of this disclosure are illustrated in FIG. 1 through FIG. 5 and FIG. 9.

Figure 1:
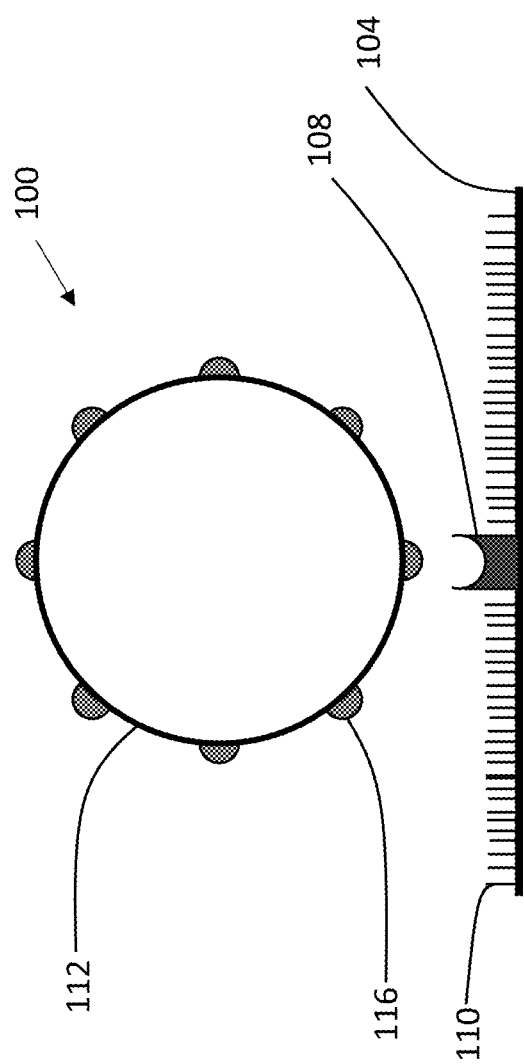
FIG. 1 is a schematic drawing (side view) that illustrates an example system of this disclosure.

FIG. 1 is a schematic drawing (side view) that illustrates an example system 100 of this disclosure. The drawing shows a substrate 104 that contains a biological particle (e.g., a cell or nucleus) capture moiety 108. A biological particle 112 may have a molecule or substance 116 (e.g., a receptor), that is able to bind to the biological particle capture moiety 108 (e.g., a ligand), resulting in retention of the biological particle 112 on the substrate 104. Multiple barcode molecules 110 are attached to the substrate 104. Generally, herein, a biological particle capture moiety 108 in combination with barcode molecules 110 associated with that biological particle capture moiety 108 can be referred to as a biological particle capture region.

Figure 2:
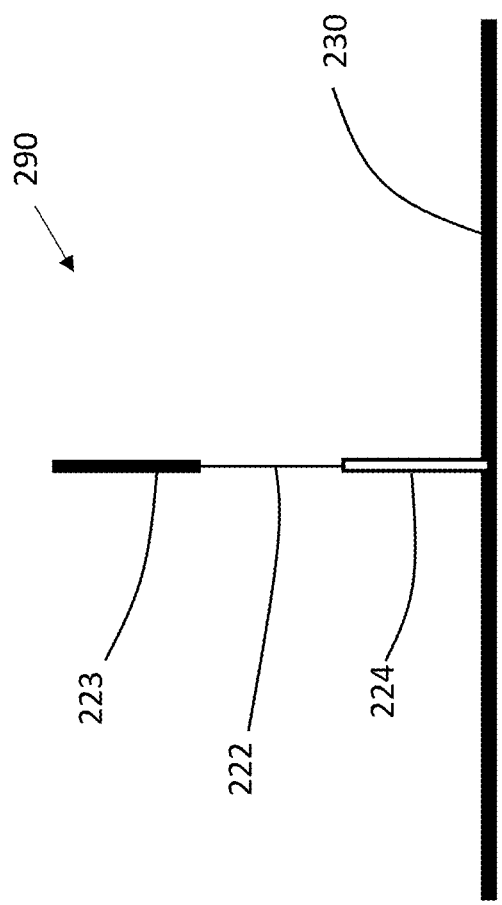
FIG. 2 is a schematic drawing (side view) that illustrates an example of a barcode molecule of this disclosure.

FIG. 2 is a schematic drawing (side view) that illustrates an example of a barcode molecule 290 of this disclosure. The barcode molecule 290 may also be called a barcoded oligonucleotide. The barcode molecule 290 is shown attached to a substrate 230. The barcode molecule 290 has a variety of regions. One region is an analyte binding sequence or analyte capture domain 223. A second region is a barcode sequence 222. The barcode sequence 222 may be common to a plurality of barcode molecules 290, a barcode sequence that corresponds to the analyte binding sequence 223, a barcode sequence that corresponds to another parameter of the system (e.g., to a cell capture region) or to something else. The barcode molecule 290 may have other regions. A barcode sequence 222 may correspond to a location on the substrate 230 where the barcode molecule 290, which may be an oligonucleotide, is attached or immobilized (e.g., spatial barcode).

A unique molecular identifier (UMI) may also be included as part of the barcoded oligonucleotide 290. A UMI sequence may correspond to a unique molecular identifier (UMI) associated with the barcoded oligonucleotide 290. The barcoded oligonucleotide 290 may have multiple barcode sequences 222. In some examples, a barcoded oligonucleotide 290 may have a barcode sequence that corresponds to the barcoded oligonucleotide 290 and a barcode sequence that corresponds to the location on the substrate 230 where the oligonucleotide is attached. The oligonucleotide may have other or additional regions 224 (e.g., PCR handles, cleavage domains, sequencing primer domains, etc.).

In some examples, referring also to FIG. 9, a nucleic acid barcode molecule 990 comprises a sequence 923 complementary to a sequence of an RNA molecule 960 from a biological particle (e.g., cell or nucleus). In some instances, sequence 923 comprises a sequence specific for an RNA molecule. In some instances, sequence 923 comprises a poly-T sequence.

In some instances, sequence 923 comprises a sequence complementary to a region of an immune molecule, such as the constant region of a TCR or BCR sequence. In one embodiment, sequence 923 comprises an analyte binding sequence, which contains nucleotide sequences that can capture, bind and/or hybridize to analytes that contain sequences encoding TCRs, TCR subunits, BCRs, antibodies, or heavy or light chains of BCRs and/or antibodies, as described herein. Sequence 923 is hybridized to RNA molecule 960 and extended via a nucleic acid reaction (e.g., a cDNA molecule 970 is generated in a reverse transcription reaction) generating a barcoded nucleic acid molecule comprising a capture region (e.g., capture region specific) barcode sequence 922 (or a reverse complement thereof) and a sequence of the extended nucleic acid (e.g., cDNA 970) (or a portion thereof). A functional sequence 921, such as a primer binding site for amplification and/or a sequencing related primer binding site (e.g., a sequence used for a sequencing reaction), etc. is also included in the barcoded oligonucleotide or capture probe. Barcoded nucleic acid molecules can then be optionally processed as described elsewhere herein, e.g., to amplify the molecules and/or append sequencing platform specific sequences to the fragments. See, e.g., U.S. Pat. Pub. No. 2018/0105808 (Ser. No. 15/825,740) which is hereby incorporated by reference in its entirety. Barcoded nucleic acid molecules, or derivatives generated therefrom, can then be sequenced on a suitable sequencing platform. Nucleic acid barcode molecule 990 may be attached to support 930 optionally via a releasable linkage 940 (e.g., comprising a labile bond), such as those described U.S. Pat. Pub. No. 2020/0063191 (Ser. No. 16/680,343), as well as WO 2020/047007A2 (Appl. No. PCT/US2019/048430), WO 2020/047010A2 (Appl. No. PCT/US2019/048434), WO 2020/047004A3 (Appl. No. PCT/US2019/048427), and WO 2020/047005A1 (PCT/US2019/048428), each of which are each incorporated by reference herein in their entirety.

Figure 3:
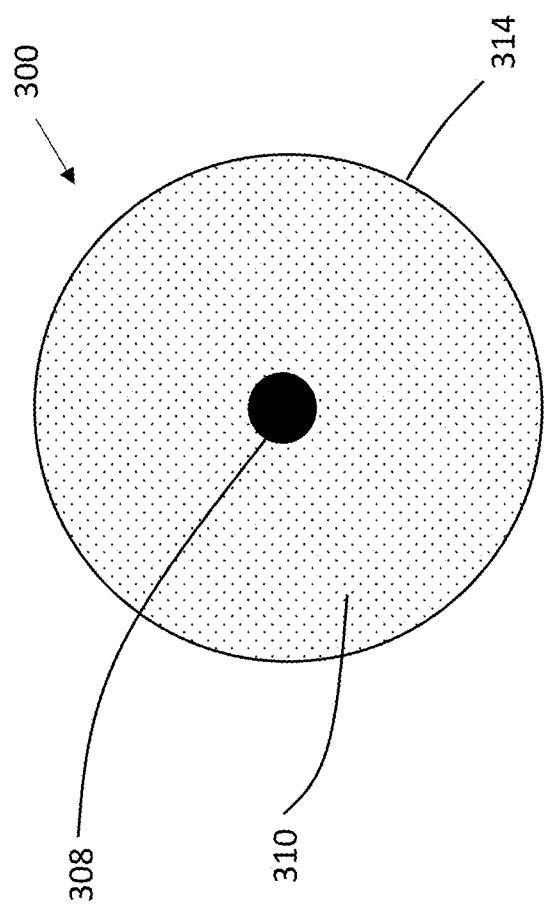
FIG. 3 is a schematic drawing (top view) that illustrates an example of a biological particle capture region of this disclosure.

FIG. 3 is a schematic drawing (top view) that illustrates an example of a biological particle capture region 300 of this disclosure. The biological particle capture region 300 contains a biological particle capture moiety 308 and a plurality of barcode molecules 310. Such a region, that contains an uninterrupted area of oligonucleotides attached to a support, may be referred to as a "demarcated region" 314. In the example, each dot 310 within the demarcated region 314 represents one or more oligonucleotides (barcode molecules) attached to the support. In some examples, the oligonucleotides 310 within the demarcated region 314 may contain the same barcode sequence that corresponds to the location on the support where the oligonucleotides 310 are attached (e.g., spatial barcode). In some examples, the oligonucleotides 310 may have analyte capture domains that may be poly(dT). In some examples, the oligonucleotides 310 within the demarcated region 314 may contain different unique molecular identifiers. In some examples, the oligonucleotides 310 within the demarcated region 314 may contain different barcode sequences that correspond to the analyte capture domain encoded by the oligonucleotide (e.g., the oligonucleotides within the demarcated region 314 may have different analyte capture domains). In some examples, the oligonucleotides 310 within the demarcated region 314 may be said to represent a species of oligonucleotides. In some examples, a species of oligonucleotides 310 may be oligonucleotides 310 with at least one barcode nucleotide sequence in common. In some examples, the barcode sequence in common may be a barcode sequence corresponding to a location on a support to which the oligonucleotides 310 are attached (e.g., spatial barcode). As described below, a support may contain multiple, adjacent demarcated regions 314. In some examples, the oligonucleotides 310 of a region may all have the same spatial barcode. In some examples, the oligonucleotides of a region may have a spatial barcode (or capture region barcode sequence—e.g., 222 in FIG. 2 or 922 in FIG. 9) that is different from the spatial barcodes of other regions, e.g., an array of biological particle capture regions on a substrate.

Referring to FIG. 3, in some examples, the biological particle (e.g., cell or nucleus) capture moiety 308 can contain substances or molecules that can bind biological particles (e.g., cells or nuclei), thus retaining biological particles on a surface of a substrate. In some examples, such substances that are part of or contained within a biological particle capture moiety can bind specific biological particles (e.g., in the case of cells, antibodies binding a cellular antigen; a receptor molecule binding a ligand for the receptor). In some examples, such substances may bind biological particles nonspecifically (e.g., in the case of cells, bind any cell). In some examples, a biological particle capture moiety 308 can contain a substance configured to interact with a labeling agent that is used to label biological particles.

Figure 4:
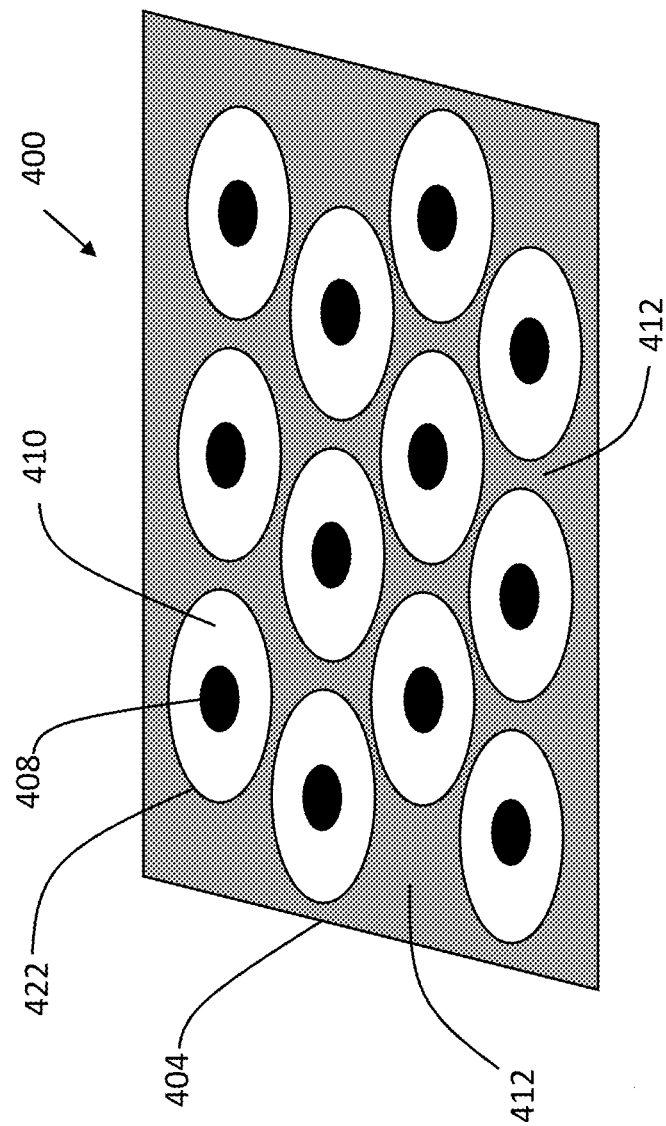
FIG. 4 is a schematic drawing (top, angular view) that illustrates an example system of this disclosure that contains multiple biological particle capture regions.

FIG. 4 is a schematic drawing (top, angular view) that illustrates an example system 400 of this disclosure that contains multiple biological particle capture regions 422. In the drawing, the substrate 404 has multiple (12 are shown) biological particle capture regions 422. The biological particle capture regions 422 have a biological particle capture moiety 408 and a plurality of barcode molecules 410 associated with the capture moiety 408. Between individual biological particle capture regions 422 are intervening regions 412, which may be of the substrate 404. Intervening regions 412 are characterized by the absence of biological particle capture moieties 422 and/or barcode molecules 410. Some example systems 400 may not have intervening regions 412 and, thus, may have continuous uninterrupted areas of barcoded oligonucleotides 410 attached to the support 404. As discussed, the biological particle capture regions 422 have biological particle capture moieties 408 and a plurality of barcode molecules 410, examples of barcode molecules which are shown in FIGS. 1 and 9, associated with the biological particle capture moiety.

Referring to FIG. 4, in some examples, the biological particle capture regions 422 can have diameters of about 5 to about 500 microns, 15 to about 150 microns, or about 30 to about 80 microns. The single biological particle capture moieties 408 can have diameters that are smaller than the diameters of the corresponding biological particle capture regions 422. For example, the biological particle capture moieties 408 can have diameters of about 0.5 to about 100 microns, or about 1 to about 15 microns, or about 5 to about. The preferred diameters can vary widely depending on the size and type of the single biological particles (e.g., cells or nuclei) being captured.

A single biological particle capture moiety 408 is applied to a portion of each biological particle capture region 422, suitably in a central region of each biological particle capture region 422 and has a diameter smaller than the diameter of the corresponding biological particle capture region 422. For example, the diameter of the single biological particle capture moiety 408 can be from about 1% to about 50% of the diameter of the corresponding biological particle capture region 422, suitably about 2% to about 25%, or about 5% to about 15% of the diameter of the barcoded spot. Each single biological particle capture moiety 408 can have a diameter that enables the capture of only one single biological particle and can have a diameter that approximates the diameter of the single biological particle being analyzed.

A single biological particle capture moiety 408 may have a chemistry (described below) that enables it to capture and hold a single biological particle in place, thereby immobilizing it. A single biological particle capture moiety 408 and the surrounding biological particle capture region 422 of which it is a part, can include a suitable nucleic acid primer (e.g., a reverse transcription primer) designed to hybridize nucleic acids (e.g., mRNA) from the captured single biological particle.

In some examples, a single biological particle capture moiety 408 and, optionally, a surrounding biological particle capture region 422 can be coated with a permeable polymer membrane (described below) to immobilize the single biological particle and its contents, to maintain any dissociated nucleic acid (e.g., mRNA) within the vicinity of the single biological particle capture site, and to prevent any dissociated nucleic acid (e.g., mRNA) from diffusing to adjacent biological particles. While most of the nucleic acid molecules (e.g., mRNA) will be contained within the single biological particle capture moiety 408, any nucleic acid molecules (e.g., mRNA) that diffuse from the capture site can be hybridized to oligonucleotides 410 that are part of the biological particle capture region 422 instead of migrating to neighboring biological particles and capture sites.

Figure 5:
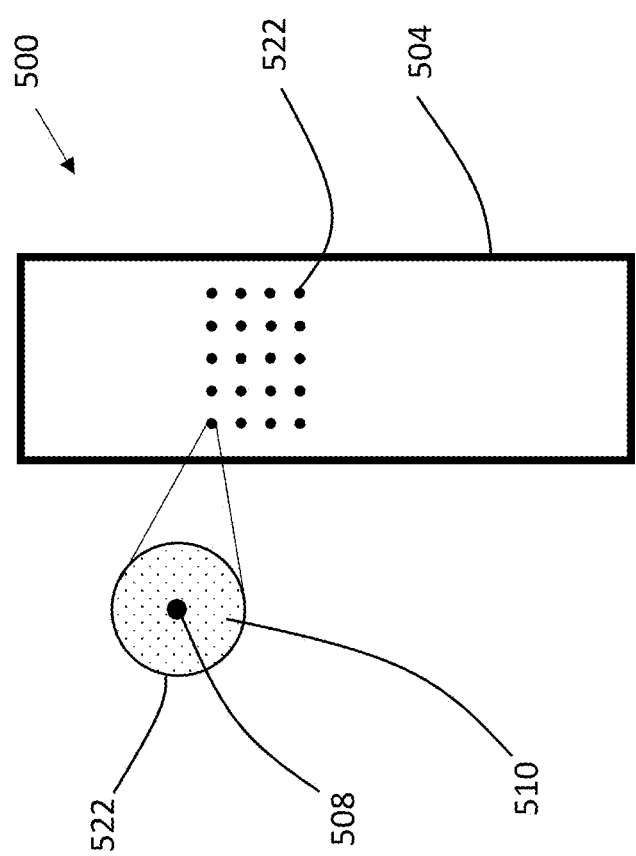
FIG. 5 is a schematic drawing (top view) that illustrates an example system of this disclosure that has multiple biological particle capture regions (inset shows expanded view of one of the biological particle capture regions).

FIG. 5 is a schematic drawing (top view) that illustrates an example system of this disclosure 500 that has multiple biological particle capture regions. The substrate 504 has multiple (20 are shown) biological particle capture regions 522. On the left side of the drawing, one of the biological particle capture regions 522 is expanded to show a biological particle capture moiety 508 and a plurality of barcode molecules 510.

Biological Particle Capture Regions

The methods and systems disclosed here use binding or attachment of single biological particles (e.g., cells or nuclei) to biological particle capture regions that have biological particle capture moieties and barcode molecules associated with the biological particle capture regions. The biological particle capture moieties retain the single biological particles.

In some examples, a biological particle capture moiety and the plurality of barcode molecules associated with it may be called a biological particle capture region. Generally, the substrates of this application contain multiple biological particle capture regions.

In some examples, the substrate may be planar or substantially planar. In some examples, the shape of the substrate may be similar to that of a microscope slide or cover slip. Example substrates may be flat and may lack microwells. Generally, the substrate is solid and example substrates may be glass or plastic. In some examples, the substrate is transparent to light. The substrates may be of various sizes and thicknesses. Dimensions of the substrates may be dictated by any instruments used to perform the methods disclosed in the application. The substrates may be configured to accept or attach biological particle capture moieties and/or components thereof. The substrates may be configured to accept or attach barcode molecules. In some examples, the substrates and/or surfaces thereof, may be coated or modified to accept the cell capture moieties and/or barcode molecules. In some examples, cell capture moieties and/or barcode molecules may be printed onto a substrate.

The substrates generally are compatible with the methods disclosed in this application. For example, biological particles (e.g., cells or nuclei) should be able to be contacted with the substrate without effects adverse to the biological particles. In some examples, biological particles may be flowed over the substrate. Biological particles that do not bind to capture moieties of the substrate should be able to be easily washed away, for example. Biological particles that do bind to capture moieties of the substrate should be able to be readily permeabilized, in some examples, to release analytes from the bound biological particles (e.g., cells or nuclei). The substrate should minimize nonspecific binding of analytes to its surface. Instead, analytes should readily be able to bind to analyte binding regions of attached barcode molecules.

Generally, biological particle capture moieties of this application are configured to bind or capture biological particles (e.g., cells or nuclei). Example biological particle capture moieties may contain substances to which cells may bind. In some examples, the capture moieties may be designed to capture specific cells and not to capture cells for which the capture moieties are not designed to capture. The capture moieties may contain substances to which some cells may bind and other cells may not bind. Example capture moieties may contain any type of molecule, including peptides, polypeptides, proteins, saccharides, polysaccharides, lipids, nucleic acids, combinations thereof, and the like.

In some examples, biological particle capture moieties may include one or more antibodies, antibody fragments or aptamers.

In some examples, the capture moieties may contain ligands to which cellular receptors may bind. Biological particles (e.g., cells or nuclei) having receptors specific for the ligands may bind, while biological particles not having the receptors or having receptors not specific for the ligand in the capture moiety may not bind.

Ligands may include those that can bind to any type of receptor, including transmembrane receptors (e.g., ligand-gated ion channels, G protein-coupled receptors, enzyme-linked hormone receptors, and the like), intracellular receptors (e.g., cytoplasmic receptors and nuclear receptors), and the like. Ligands may include any type of molecule like, for example, proteins, peptides, other small molecules (e.g., neurotransmitters, hormones, pharmaceutical drug, toxin, calcium ion, or parts of microorganisms, like viruses or bacteria), and the like. Ligands may be agonists. Ligands may be antagonists.

Biological particle capture moieties may be designed to capture any type of cell. In some examples, cells designed to be captured may be cells from the immune system. For example, the capture moieties may be designed to contain molecules that capture or will be bound by lymphocytes, mononuclear phagocytes, dendritic cells, granulocytes, and the like. Lymphocytes may include T-cell lymphocytes or B-cell lymphocytes. Example T-cell lymphocytes may include CD4+ T-cell lymphocytes or CD8+ T-cell lymphocytes.

Biological particle capture moieties designed to capture T-cell lymphocytes may contain peptides to which T-cell receptors (TCRs) and/or one or both of TCR subunits, TCRα and TCRβ, on the T-cell lymphocytes may specifically bind. The peptides may be T-cell epitopes from various antigens. The peptides may be T-cell epitopes from specific antigens. The peptides may be chosen to test the ability of the specific peptide amino acid sequence to act as a T-cell epitope. Peptides used may be of various amino acid lengths. In some examples, the peptides may be between 2 and 100 amino acids in length, 5 and 50 amino acids in length, 6 and 30 amino acids in length, 6 and 20 amino acids in length or 6 and 18 amino acids in length. In some examples, the peptides may have 5, 6, 7, 8, 9, 10, 11, 12, 13, 14, 15, 16, 17, 18, 19, 20, 21, 22, 23, 24, 25, 26, 27 or 28 amino acids.

In some examples, where peptides are used to capture T-cell lymphocytes, the capture moieties may contain the peptide and at least one other molecule. In some examples, the additional molecule may be a major histocompatibility complex (MHC) molecule. In some examples, the additional molecule may be an MHC class I (MHC-I) molecule and/or an MHC class II (MHC-II) molecule. The MHC molecules may be combined with the peptide or peptides in a manner such that a TCR specific for the particular peptide can bind to the peptide that is part of the capture moiety. In some examples, the particular MHC molecules used may be an MHC multimer that contains the peptide. In some instances, the particular MHC molecules/MHC multimers used in the capture moieties may be similar to or "matched" to the MHC molecules on the T-cell lymphocytes that are desired to be captured. There are many possible configurations of Class I and/or Class II MHC multimers that can be utilized with the compositions, methods, and systems disclosed herein, e.g., MHC tetramers, MHC pentamers (MHC assembled via a coiled-coil domain, e.g., Pro5® MHC Class I Pentamers, (ProImmune, Ltd.), MHC octamers, MHC dodecamers, MHC decorated dextran molecules (e.g., MHC Dextramer® (Immudex)), etc. For a description of exemplary MHC multimers and methods of use, see, e.g., U.S. Pat. No. 10,550,429 (Ser. No. 16/426,762) and U.S. Pat. Publ. No. 2019/0367969 (Ser. No. 16/375,093), which are each incorporated by reference herein in their entirety. In some examples, cell capture moieties do not contain cells (e.g., they are cell-free). Rather, the cell capture moieties contain molecules and/or combinations of molecules that may be from cells.

Biological particle capture moieties designed to capture B-cell lymphocytes may contain antigens or peptides to which B-cell receptors (BCRs) and/or heavy or light chains from BCRs, may specifically bind. In some examples, the peptides may be between 2 and 100 amino acids in length, 5 and 50 amino acids in length, 6 and 30 amino acids in length, 6 and 20 amino acids in length or 6 and 18 amino acids in length. In some examples, the peptides may have 5, 6, 7, 8, 9, 10, 11, 12, 13, 14, 15, 16, 17, 18, 19, 20, 21, 22, 23, 24, 25, 26, 27 or 28 amino acids.

In some embodiments, the capture region comprises a nucleic acid barcode molecule that contains a labeling agent sequence that is configured to interact with a labeling agent that is used to label biological particles (e.g., cell or nuclei). For instance, a population of single immune cells can be labeled with a labeling agent before or after contacting with the substrate. Such a labeling agent sequence can include a specific sequence that is complementary to a reporter oligonucleotide sequence conjugated to a labeling agent (e.g., an antibody). The reporter oligonucleotide sequence corresponds to the labeling agent used to label the single immune cells. The labeling agent sequence can prime a nucleic acid extension reaction to generate a nucleic acid molecule comprising the reporter oligonucleotide sequence, or a complement thereof. In some embodiments, the labeling agent sequence comprises a sequence that is the same as or is different than the analyte binding sequence (e.g., sequence 923 in FIG. 9).

In some instances, one or more labelling agents capable of binding to or otherwise coupling to one or more cell features may be used to characterize immune cells and/or immune cell features. In some instances, immune cell features include cell surface features. Cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429 (Ser. No. 16/426,762); U.S. Pat. Publ. No. 2019/0177800 (Ser. No. 16/107,685); and U.S. Pat. Pub. Publ. No. 2019/0367969 (Ser. No. 16/375,093), which are each incorporated by reference herein in their entirety.

In some examples, a suitable labeling technique, known as biotinylation, may be accomplished by covalently attaching a biotin to a protein, nucleic acid, or other molecule in the biological particle being analyzed. The biotin can then bind to a selectively designed capture moiety with high affinity, speed and specificity. Various kinds of biotinylation include enzymatic biotinylation which allows biotin to be linked to a residue present in a protein, primary amine biotinylation which involves linkage of biotin to primary amine groups in the protein, sulfhydryl biotinylation which attaches biotin to sulfhydryl groups in the protein, carboxyl biotinylation which attaches biotin to carboxyl groups on the C-terminal ends of proteins and on glutamate and aspartate amino acid side chains, glycoprotein biotinylation which modifies the carbohydrate residues in glycoprotein to aldehydes that react with hydrazine- or alkoxyamine-based biotinylation reagents, oligonucleotide biotinylation which reacts oligonucleotides with biotin phosphoramidite, and non-specific biotinylation using photoactivatabe biotin reagents. One example of a suitable biotin molecule for binding the single cells or nuclei to the cell or nuclei capture sites is cholesterol-biotin.

Biotins bind easily to streptavidin, avidin and neutravidin protein molecules and such bonds are resistant to extreme heat, pH and proteolysis. This makes it possible to capture biotinylated molecules, and cells or nuclei stained with biotins, in a wide range of environments.

A variety of other molecular pairs can be used to bind cells to cell capture moieties. In some examples, the pairs may include glutathione and glutathione S-transferase, maltose and maltose-binding protein, and the SpyTag/SpyCatcher™ system, and the like. In some examples, antibodies designed to bind cells or specific types of cells may be part of the cell capture moiety.

In some instances, one or more labelling agents capable of binding to or otherwise coupling to one or more biological particle (e.g., cell or nucleus) features may be used to bind biological particles to a biological particle capture moiety. In some instances, biological particle features can include biological particle surface features. In the case of cells, cell surface features may include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

Barcoded Oligonucleotides of Biological Particle Capture Regions

Example barcode molecules disclosed in this application may have one or more barcodes, e.g., barcode nucleic acid sequences. Example barcode molecules may have one or more analyte binding sequences. In some examples, a plurality of barcode molecules may be associated with one or more cell capture moieties. The combination of the one or more biological particle capture moieties and the barcode molecules associated with the biological particle capture moieties may be referred to as a biological particle capture region. In some examples, barcode molecules associated with one or more capture moieties, and that make up a single capture region, are arranged such that analytes released from biological particles that bind the capture moiety or moieties of the capture region diffuse from the biological particles such that they contact the barcode molecules (e.g., via the analyte binding sequences) associated with the particular capture moiety or moieties of the capture region, and do not diffuse such that they contact barcode molecules associated with other capture regions. In some examples, a biological particle capture region may contain about $10^3$, $10^4$, $10^5$, $10^6$, $10^7$, $10^8$ or $10^9$ barcode molecules associated with the capture moiety or moieties of the capture region. In some examples, a capture region may be between about 10 and $10^3$ µm across, or between about 10 and $10^3$ µm from a first border or edge to a second border or edge directly across from the first. In some examples, the plurality of barcode molecules associated with a particular biological particle capture moiety or moieties, or that are part of a single biological particle capture region, are within about 10 to $10^6$ µm of each other. In some examples, a distance between adjacent biological particle capture regions may be between about 1 and $10^2$ µm. In some examples, a substrate may contain between about $10^3$ and $10^8$ capture regions. In some examples, a polymer coating may be applied to the substrate after biological particle capture, such that analytes released from biological particles bound by one capture region are unable to diffuse to a second capture region.

Analyte binding sequences of barcode molecules may be configured to bind analytes from a biological particle (e.g., cells or nuclei). Analyte binding sequences may be configured to bind specific analytes from a biological particle, such that analytes that a particular analyte binding sequence is not configured to bind are not bound. Analyte binding sequences may be designed to bind any type of molecule. For example, analyte binding sequences may be designed to bind proteins, polysaccharides, lipids, nucleic acids, and the like.

The systems disclosed in this application may be used to detect many different types of analytes. Biological particle analytes that are suitable for use with the systems of this disclosure include, without limitation, intracellular and extracellular analytes. A cellular analyte may be a protein, a metabolite, a metabolic byproduct, an antibody or antibody fragment, an enzyme, an antigen, a carbohydrate, a lipid, a macromolecule, or a combination thereof (e.g., proteoglycan) or other biomolecule. A cellular analyte may be a nucleic acid molecule. A cellular analyte may be a deoxyribonucleic acid (DNA) molecule or a ribonucleic acid (RNA) molecule. A DNA molecule may be a genomic DNA molecule. A cellular analyte may comprise coding or non-coding RNA. An RNA may be messenger RNA (mRNA), ribosomal RNA (rRNA) or transfer RNA (lRNA), for example. An RNA may be a transcript. An RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). An RNA may be double-stranded RNA or single-stranded RNA. An RNA may be circular RNA.

In one embodiment, the cellular analyte may be a complementary DNA (cDNA) that is reverse transcribed from an mRNA molecule of the biological particle (e.g., a cell or a nucleus). The reverse transcription may take place using a reverse transcriptase and a free primer comprising a poly-T capture sequence and can include template switching. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA.

FIGS. 10A and 10B illustrate one example of the reverse transcription of cDNA 1070 from an RNA molecule 1060 (e.g., an mRNA molecule), which includes the step of adding several non-templated bases 1080. The sequence of non-templated bases is complementary to a sequence on the nucleic acid barcode molecule 1090 that is coupled to the substrate, e.g., at an analyte capture region. For example, referring to FIG. 10A, panel 1001, in some embodiments, primer 1050 comprises a sequence complementary to a sequence of nucleic acid molecule 1060 (such as an RNA encoding for a BCR or a TCR sequence) from a biological particle (e.g., a cell or a nucleus). In some instances, primer 1050 comprises one or more sequences 1051 that are not complementary to RNA molecule 1060. Sequence 1051 may be a functional sequence as described elsewhere herein, for example, an adapter sequence, a sequencing primer sequence, or a sequence the facilitates coupling to a flow cell of a sequencer. In some instances, primer 1050 comprises a poly-T sequence. In some instances, primer 1050 comprises a sequence complementary to a target sequence in an RNA molecule. In some instances, primer 1050 comprises a sequence complementary to a region of an immune cell receptor, such as the constant region of a TCR or BCR sequence. Primer 1050 is hybridized to nucleic acid molecule 1060 and complementary molecule 1070 is generated (see Panel 1002 in FIG. 10B). For example, complementary molecule 1070 may be cDNA generated in a reverse transcription reaction. In some instances, an additional sequence may be appended to complementary molecule 1070. For example, the reverse transcriptase enzyme may be selected such that several non-templated bases 1080 (e.g., a poly-C sequence) are appended to the cDNA. In another example, a terminal transferase may also be used to append the additional sequence. Nucleic acid barcode molecule 1090 comprises a sequence 1024 complementary to the non-templated bases, and the reverse transcriptase performs a template switching reaction onto nucleic acid barcode molecule 1090 to generate a barcoded nucleic acid molecule comprising a biological particle (e.g., biological capture region specific) barcode sequence 1022 (or a reverse complement thereof) and a sequence of complementary molecule 1070 (or a portion thereof). In some instances, sequence 1023 comprises a sequence complementary to a region of an immune cell receptor, such as the constant region of a TCR or BCR sequence. Sequence 1023 is hybridized to nucleic acid molecule 1060 and a complementary molecule 1070 is generated. For example, complementary molecule 1070 may be generated in a reverse transcription reaction generating a barcoded nucleic acid molecule comprising a biological particle (e.g., biological capture region specific) barcode sequence 1022 (or a reverse complement thereof) and a sequence of complementary molecule 1070 (or a portion thereof). Additional methods and compositions suitable for barcoding cDNA generated from mRNA transcripts including those encoding V(D)J regions of an immune cell receptor and/or barcoding methods and composition including a template switch oligonucleotide are described in International Patent Application WO 2018/075693, U.S. Patent Publication No 2018/0105808, U.S. Patent Publication No. 2015/0376609, filed Jun. 26, 2015, and U.S. Patent Publication No. 2019/0367969, each of which applications is herein entirely incorporated by reference for all purposes.

In some instances, an analyte from a biological particle may be associated with an intermediary entity, wherein the intermediary entity is analyzed to provide information about the cellular analyte and/or the intermediary entity itself. For instance, an intermediary entity (e.g., an antibody) may be bound to an extracellular analyte (e.g., a cell surface receptor), where the intermediary entity is processed to provide information about the intermediary entity, the extracellular analyte, or both. In one embodiment, the intermediary entity comprises an identifier (e.g., a barcode).

In some examples, analyte binding sequences contain nucleotide sequences that can capture other, complementary nucleotide sequences, through hybridization. In some examples, the complementary nucleotide sequences are part of an analyte from a biological particle (e.g., cells or nuclei) that include DNA, RNA, mRNA, sequences that are complementary to sequences in the DNA, RNA or mRNA, or amplification products from the DNA, RNA or mRNA or their complementary sequences.

In some examples, analyte binding sequences may contain nucleotide sequences that can capture, bind and/or hybridize to analytes that contain sequences encoding TCRs, TCR subunits, BCRs, antibodies, or heavy or light chains of BCRs and/or antibodies. In some examples, analyte binding sequences may contain nucleotide sequences that can capture, bind and/or hybridize to analytes that contain sequences encoding TCRs, TCR subunits, BCRs, antibodies, or heavy or light chains of BCRs and/or antibodies of the cells that a cell capture moiety is designed to capture. In some examples, these analyte binding sequences may contain rearranged V(D)J sequences. In some examples, the rearranged V(D)J sequences used in an analyte binding sequence of a barcode molecule may be a sequence, or a sequence complementary to, a sequence that encodes a TCR, TCR subunit, BCR or heavy or light chain of a BCR that is part of a cell that a particular cell capture moiety is designed to capture.

Barcode molecules disclosed in this application may contain barcodes or barcode sequences. A barcode molecule may contain 1, 2, 3, 4, 5 or more different barcodes. The barcodes present in distinct barcode molecules may be unique to the barcode molecule or may be common between two or more barcode molecules. In some examples, the barcode molecules that are part of a cell capture region have a common barcode. Such a common barcode may be used to determine whether an analyte bound by an analyte binding sequence of a barcode molecule is from cells captured by cell binding moieties from that particular cell capture region or from cells captured by cell binding moieties from a different cell capture region. In some examples, barcode molecules have unique barcodes associated with each different analyte binding sequences. Such a barcode may be used to determine the identity of an analyte bound or captured by a particular barcode molecule. In some examples, each barcode molecule has a unique barcode. Such unique barcodes may be used, for example, together with barcodes unique to common analyte binding sequences, to determine how much of a specific analyte is present in individual cells or in a group of cells captured or retained by the systems and methods disclosed in this application.

Referring to FIG. 4, the barcoded oligonucleotides 410 of the biological particle (e.g., cell or nucleus) capture regions 422 can be designed to perform at least two functions, labelling and hybridization. The at least two functions can be performed by using a single barcoded primer (e.g., a reverse transcription primer), which facilitates hybridization and comprises a barcode (e.g., a nucleic acid barcode sequence), or by using separate barcoding (labeling) and a primer (e.g., a reverse transcription primer for hybridization) materials. In other words, for instance, the biological particle capture regions 422 can include a barcoded reverse transcription primer, or some combination of a reverse transcription primer and a barcode material (e.g., a nucleic acid barcode sequence).

The barcoded oligonucleotides 410 of the biological particle capture regions 422 can be formed using any suitable barcode material (e.g., nucleic acid barcode molecules) that can be printed or otherwise formed as barcodes in the demarcated regions 422 on the surface of the substrate 404. The barcodes can be a label or other identifier that conveys or is capable of conveying information, e.g., information about the mRNA in the single biological particles (e.g., single cells or nuclei) being analyzed. The barcodes can have a variety of different chemistries. For example, the barcodes can include polynucleotide barcodes, random nucleic acid and/or amino acid sequences, synthetic nucleic acid and/or amino acid sequences, or any combination of the foregoing. The barcodes can allow for identification and/or quantification of individual sequencing-reads, e.g., a barcode can be or can include a unique molecular identifier or "UMI." In some embodiments, a barcode can include two or more sub-barcodes that together function as a single barcode. For example, a polynucleotide barcode can include two or more polynucleotide sequences or sub-barcodes that are separated by one or more non-barcode sequences. A barcode can be a fluorescent barcode to which fluorescently labeled oligonucleotides hybridize. A barcode can be attached to an mRNA molecule or other oligonucleotide.

The barcode sequences can include from about 6 to about 20 or more nucleotides. In some embodiments, the length of a barcode sequence can be about 6, 7, 8, 9, 10, 11, 12, 13, 14, 15, 16, 17, 18, 19, 20 nucleotides or longer. In some embodiments, the length of a barcode sequence is at most about 6, 7, 8, 9, 10, 11, 12, 13, 14, 15, 16, 17, 18, 19, 20 nucleotides or shorter. The nucleotides can be completely contiguous, e.g., in a single stretch of adjacent nucleotides, or they can be separated into two or more subsequences that are separated by one or more nucleotides. Separated spatial barcode subsequences can be from about 4 to about 16 nucleotides in length. In some embodiments, the separated barcode subsequence can be about 4, 5, 6, 7, 8, 9, 10, 11, 12, 13, 14, 15, 16 nucleotides or longer. In some embodiments, the separated barcode subsequence can be at most about 4, 5, 6, 7, 8, 9, 10, 11, 12, 13, 14, 15, 16 nucleotides or shorter.

The barcoded oligonucleotides 410 of the biological particle capture regions 422 can include a nucleic acid primer (e.g., a reverse transcription primer) that includes a functional nucleic acid sequence (herein "oligonucleotide domain") configured to interact with the target analyte (e.g., mRNA molecules) in the single biological particle being analyzed, and to hybridize to the target analyte for further processing (e.g., reverse transcription of an mRNA target analyte to yield cDNA. The primer (e.g., a reverse transcription primer) can be barcoded to include all or a portion of the foregoing barcode materials, can be chemically attached to the barcodes, or can be applied to the barcoded spots separate from the barcode materials.

In one embodiment, the functional nucleic acid sequence of the reverse transcription primer can include a poly(T) sequence that is configured to interact with the mRNA molecules via the poly(A) tail of an mRNA transcript. In the present invention, any such primer (e.g., the reverse transcription primer) can include capture domains (referred to herein as "oligonucleotide domains") such as ribonucleotides and/or deoxyribonucleotides as well as synthetic nucleotide residues that can participate in Watson-Crick type or analogous base pair interactions with the target mRNA. The oligonucleotide domains can prime a reverse transcription reaction to generate cDNA that is complementary to the target mRNA molecules. The oligonucleotide domains can be ligated to one strand of the target mRNA molecules. For example, SplintR ligase along with RNA or DNA sequences (e.g., degenerate RNA) can be used to ligate a single-stranded mRNA to an oligonucleotide domain. In some embodiments, ligases with RNA-templated ligase activity, e.g., SplintR ligase, T4 RNA ligase 2 or KOD ligase, can be used to ligate a single-stranded mRNA to the oligonucleotide domain.

In some embodiments, an oligonucleotide domain of the reverse transcription primer includes a splint oligonucleotide. An oligonucleotide domain can include a free 3' end that can be extended, e.g., by template dependent polymerization, to form an extended oligonucleotide domain. The oligonucleotide domain can be selected or designed to bind selectively or specifically to a target mRNA by way of hybridization to the mRNA poly(A) tail. Thus, the oligonucleotide domain can include a poly(T) DNA oligonucleotide, e.g., a series of consecutive deoxythymidine residues linked by phosphodiester bonds, which is capable of hybridizing to the poly(A) tail of mRNA. The oligonucleotide domain can include oligonucleotides that are functionally or structurally analogous to a poly(T) tail, for example, a poly(U) oligonucleotide or an oligonucleotide including deoxythymidine analogues. The oligonucleotide domain can have any sequence that is capable of binding to mRNA. In some embodiments, a homopolymer sequence is added to an mRNA molecule using a terminal transferase enzyme in order to produce a molecule having a poly(A) or poly(T) sequence. For example, a poly(A) sequence can be added to an mRNA, thereby making the mRNA capable of capture by a poly(T) oligonucleotide domain.

In some embodiments, random sequences, e.g., random hexamers or similar sequences, can be used to form all or a part of the oligonucleotide domain. For example, random sequences can be used in conjunction with poly(T) (or poly(T) analogue) sequences. Thus, when the oligonucleotide domain includes a poly(T) (or a "poly(T)-like") oligonucleotide, it can also include a random oligonucleotide sequence (e.g., "poly(T)-random sequence" probe). This can, for example, be located at 5' or 3' of the poly(T) sequence, e.g., at 3' end of the oligonucleotide domain. The poly(T)-random sequence can facilitate the capture of the mRNA poly(A) tail. In some embodiments, the oligonucleotide domain can be an entirely random sequence. In some embodiments, degenerate oligonucleotide domains can be used.

In some embodiments, a pool of two or more oligonucleotide domains form a mixture, where one oligonucleotide domain includes a poly(T) sequence and another oligonucleotide domain includes random sequences. In some embodiments, a pool of two or more oligonucleotide domains form a mixture where the one oligonucleotide domain includes a poly(T)-like sequence and another oligonucleotide domain includes random sequences. In some embodiments, a pool of two or more oligonucleotide domains form a mixture where one oligonucleotide domain includes a poly(T)-random sequences and another oligonucleotide domain includes random sequences. In some embodiments, degenerate oligonucleotide domains can be added to any of the preceding combinations listed herein. In some embodiments, degenerate oligonucleotide domains can be substituted for one of the oligonucleotide domains in each of the pairs described herein.

The oligonucleotide domain of the reverse transcription primer can be based on a gene sequence, a motif sequence or common/conserved sequence that it is designed to capture (i.e., a sequence-specific oligonucleotide domain). Thus, the oligonucleotide domain can be capable of binding selectively to a desired sub-type or subset of nucleic acid, for example a type or subset of mRNA. In some embodiments, the oligonucleotide domain includes an "anchor" or "anchoring sequence," which is a sequence of nucleotides designed to ensure that the oligonucleotide domain captures and hybridizes to the intended mRNA. The anchor sequence can include a sequence of nucleotides, including a 1-mer, 2-mer, 3-mer or longer sequence. The sequence can be random. For example, an oligonucleotide domain including a poly(T) sequence can be designed to capture an mRNA. An anchoring sequence can include a random 3-mer (e.g., GGG) that helps ensure that the poly(T) oligonucleotide domain hybridizes the mRNA. In some embodiments, an anchoring sequence can be VN, N, or NN. Alternatively, the sequence can be designed using a specific sequence of nucleotides. In some embodiments, the anchor sequence is at the 3' end of the oligonucleotide domain. In some embodiments, the anchor sequence is at the 5' end of the oligonucleotide domain.

In one additional embodiment, the biological particle capture regions 422 comprise a proteomic nucleic acid primer sequence that is configured to interact with a protein labeling agent that is used to label a population of single biological particles (e.g., single cells or single nuclei) before or after contacting with the substrate. Such proteomic nucleic acid primer sequences can include a specific sequence that is complementary to a reporter oligonucleotide sequence conjugated to a protein labeling agent (e.g., an antibody). The reporter oligonucleotide sequence corresponds to the protein labeling agent used to label the single biological particles. The proteomic nucleic acid primer sequence can prime a nucleic acid extension reaction to generate a nucleic acid molecule comprising the reporter oligonucleotide sequence, or a complement thereof. Additional methods and compositions concerning labeling agents with reporter oligonucleotides (comprising reporter sequences) are provided in WO2018/119447, WO2019/157529, US20190338353, US20200002763, and US20190323088 each of which is incorporated by reference in its entirety.

Methods

Figure 6:
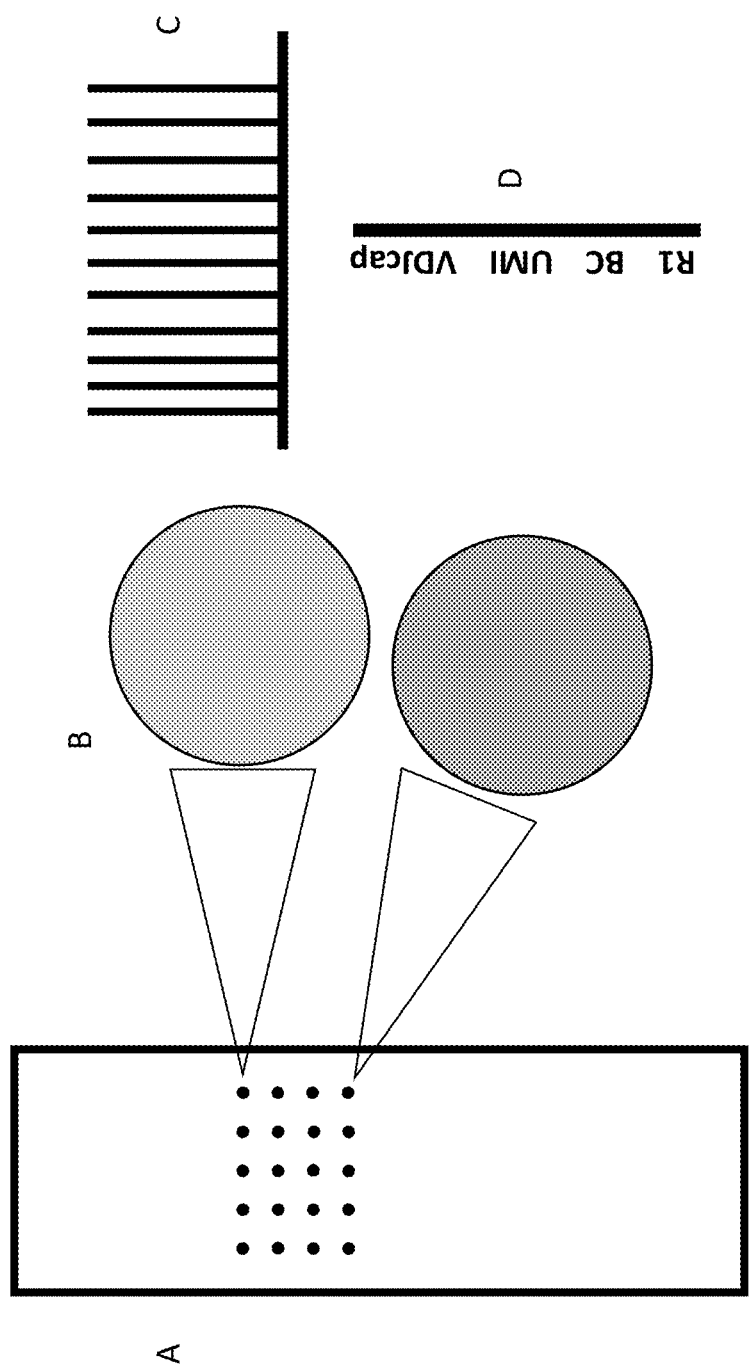
FIG. 6 is a schematic drawing that illustrates (A) a top view of an example system that has multiple biological particle capture regions, similar to FIG. 5; (B) expanded top views of two separate biological particle capture regions on the substrate, similar to FIGS. 3 and 4; (C) a side view of a plurality of barcode molecules attached to the substrate, similar to FIG. 1; and (D) a side view of a single barcode molecule attached to the substrate, similar to FIG. 2, showing example regions of the barcode molecule.
Figure 7:
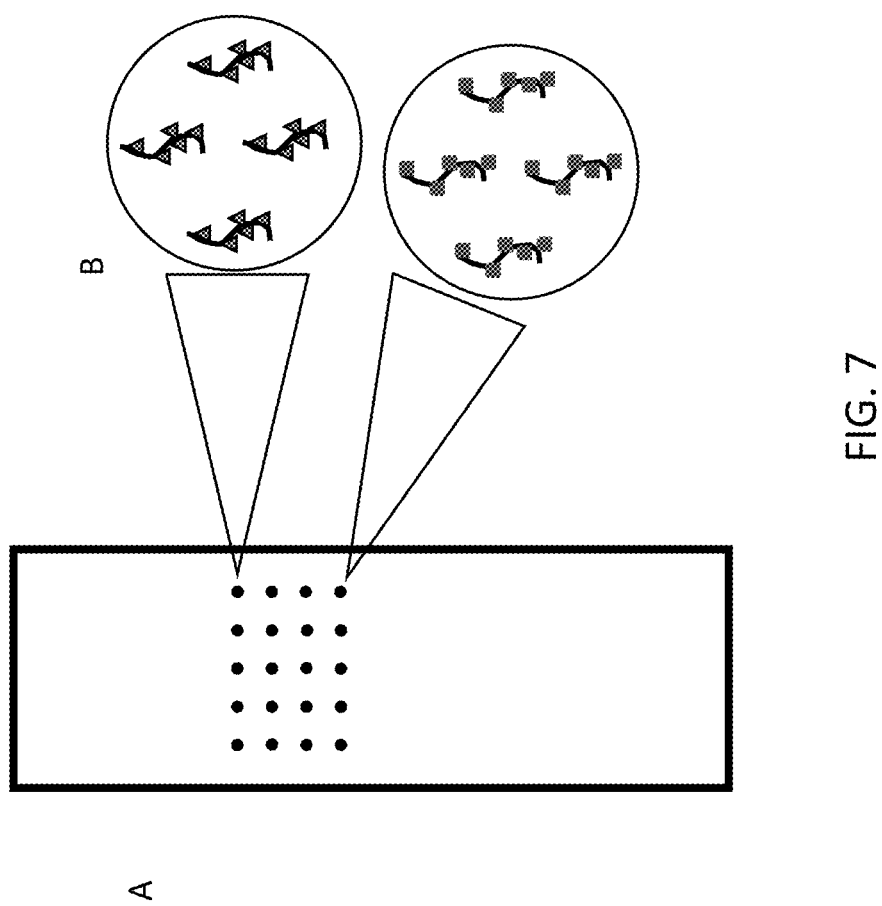
FIG. 7 is a schematic drawing (top view) that illustrates (A) a panel similar to that of FIG. 6A. The (B) panel of this drawing represents example MHC multimers of two different biological particle capture regions. The top cell capture region contains MHC multimers in combination with a specific peptide epitope (triangles). The bottom cell capture region contains MHC multimers in combination with a specific peptide epitope (squares) that is different than the peptide epitope of the top biological particle capture region.
Figure 8:
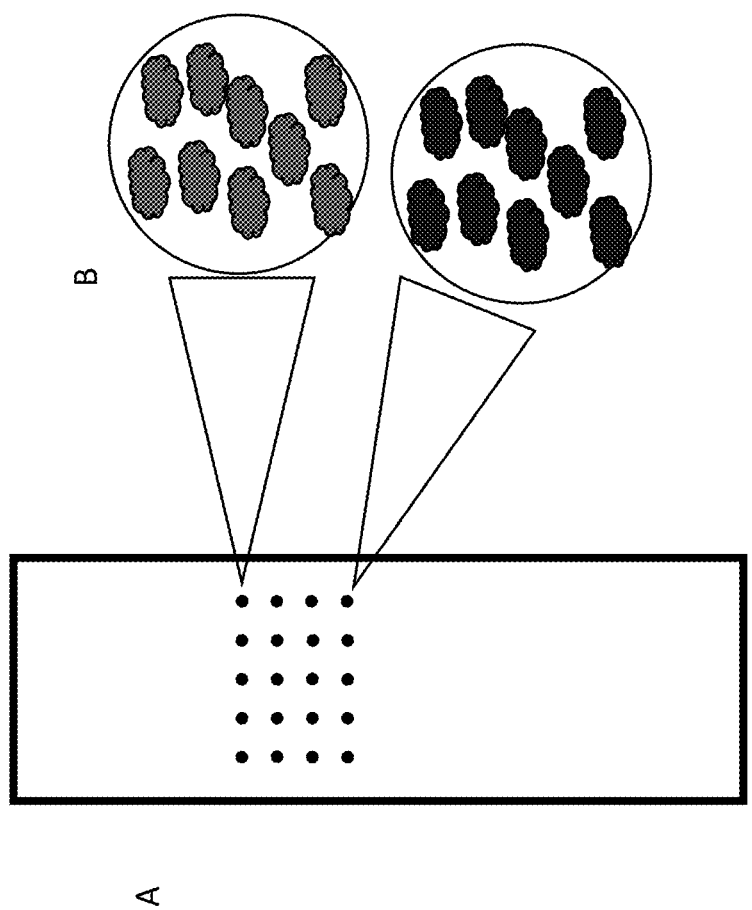
FIG. 8 is a schematic drawing (top view) that illustrates (A) a panel similar to those of FIGS. 6A and 7A. The (B) panel of this drawing represents example T-cell lymphocytes that have bound to or been captured by the MHC multimers and peptides as shown in FIG. 7B. The top biological particle capture region in (B) shows T-cell lymphocytes containing TCRs specific for binding the MHC multimers in combination with the first specific peptide epitope (triangles in top biological particle capture region of FIG. 7B) that have bound to the biological particle capture moieties of the top biological particle capture region. The bottom biological particle capture region in (B) shows T-cell lymphocytes containing TCRs specific for binding the MHC multimers in combination with the second specific peptide epitope (squares in bottom biological particle capture region of FIG. 7B) that have bound to the biological particle capture moieties of the bottom biological particle capture region.

Various examples of the methods of this disclosure are illustrated in FIG. 6 through FIG. 8.

FIG. 6 is a schematic drawing that illustrates various features of an example system of the invention. Panel (A) is a top view of a substrate that has multiple biological particle capture regions, similar to that shown in FIG. 5. Panel (B) is an expanded top view of two separate biological particle capture regions of the substrate, similar to those shown in FIGS. 3 and 4. Panel (C) is a side view of a plurality of barcode molecules attached to the substrate, similar to that shown in FIG. 1. Panel (D) is a side view of a single barcode molecule attached to the substrate, showing example regions of the barcode molecule. "VDJ cap" represents an example analyte binding sequence of the barcode molecule that contains an analyte binding sequence capable of binding a rearranged V(D)J sequence of a T-cell receptor from a cell. In this drawing, the specific rearranged V(D)J capture sequences for the top cell capture region in panel (B) are different than the specific rearranged V(D)J capture sequences for the bottom cell capture region in panel (B) (i.e., the rearranged V(D)J sequences captured will be different). In panel (D), "BC" represents a barcode sequence common to all barcode molecules associated with a specific cell capture region. "UMI" represents a barcode sequence unique to each barcode molecule.

FIG. 7 is a schematic drawing that is a continuation of FIG. 6. Panel (A) is a top view of a substrate that has multiple cell capture regions, similar to that shown in FIG. 6A. Panel (B) represents MHC multimers of two different cell capture regions. The top cell capture region contains MHC multimers in combination with a specific peptide epitope (triangles). The bottom cell capture region contains MHC multimers in combination with a specific peptide epitope (squares) that is different than the peptide epitope of the top cell capture region.

FIG. 8 is a schematic drawing that is a continuation of FIG. 7. Panel (A) is a top view of a substrate that has multiple cell capture regions, similar to that shown in FIGS. 6A and 7A. Panel (B) represents T-cell lymphocytes that have bound to or been captured by the MHC multimers and peptides as shown in FIG. 7B. The top cell capture region in (B) shows T-cell lymphocytes containing TCRs specific for binding the MHC multimers in combination with the first specific peptide epitope (triangles in top cell capture region of FIG. 7B) that have bound to the cell capture moieties of the top cell capture region. The bottom cell capture region in (B) shows T-cell lymphocytes containing TCRs specific for binding the MHC multimers in combination with the second specific peptide epitope (squares in bottom cell capture region of FIG. 7B) that have bound to the cell capture moieties of the bottom cell capture region. The TCRs, and thus the T-cell lymphocytes, that have bound to the top cell capture region are different than the TCRs and T-cell lymphocytes that have bound to the bottom cell capture region. The example depicted in FIGS. 6-8 can be adapted for B cell analysis. In particular, the substrate may comprise one or more antigens (instead of MHC multimers in combination with a specific peptide epitope) at the cell capture regions. This antigen array may be used to capture B cells expressing B cell receptors (BCRs) that are specific for the antigens on the array. The captured B cells can be further processed at the capture sites as further described herein.

Generally, the methods disclosed in this application are designed to capture biological particles (e.g., cells or nuclei) on a substrate and to analyze the analyte composition of the captured biological particles, on a single-particle basis. The systems disclosed are configured to capture biological particles, and the systems can be configured to capture specific biological particles from a biological particle population (e.g., through the composition of the biological particle capture moieties), and not to capture other biological particles within the same population. Therefore, the disclosed systems and methods can be used to correlate specific biological particle-binding events, and/or the molecules involved in those events, with specific analytes from biological particles engaged in the binding.

One example of this is selecting and retaining immune cells that bind to peptides having specific amino acid sequences contained within cell binding moieties of the disclosed systems, and efficiently determining the sequence of the receptor on the immune cell that is responsible for binding the specific peptide. The system and methods can be manipulated such that cells having different binding affinities for a target can be analyzed. Imaging and/or visualization can be used to determine numbers of cells bound to various cell capture regions, morphologies and/or cell types of the captured cells. Cell staining can be incorporated into this component of the methods. Cells captured and retained on the substrate may be propagated, on the substrate for example. These embodiments of the disclosed methods could be used as diagnostic tests to determine, for example, whether T- and/or B-cells that bind to a specific ligand are present in certain populations of cells.

In some examples of the disclosed methods, a population of biological particles is contacted with the systems disclosed in this application. The biological particle population can be enriched for certain biological particles (e.g., cell types), or the biological particle population can contain multiple biological particle types (e.g., cell types). The disclosed methods are such that specific biological particle binding and retention of the biological particles may be used to select biological particles, which may be rare biological particles, from the initial biological particle population.

Attachment of Biological Particles to Capture Moieties

Attachment of the single biological particles (e.g., cells or nuclei) to a biological particle capture moiety can be accomplished by any suitable means and may depend on the specific chemistry and design of the biological particles and the biological particle capture moieties.

Generally, a single biological particle (e.g., a cell or nucleus) is to be retained by one biological particle capture moiety. In that way, barcoded oligonucleotides having capture domains that surround the biological particle capture moiety can capture analytes from the single retained biological particle.

In some examples, applying a suspension of the biological particles to a surface containing the biological particle capture regions and capture moieties, the surface can be effectively contacted with single biological particles bound to individual biological particle capture moieties.

In examples in which the biological particles are cells, cell contacting with the surface and biological particle capture moieties can be performed by flowing a population of cells over the disclosed systems. By adjusting the concentration of biological particles in a liquid, one can increase the probability that a biological particle capture moiety will retain a biological particle and will not retain greater than one biological particle (e.g., Poisson statistics). In some examples, the biological particle capture moieties may be designed such that, once a single biological particle is retained by the biological particle capture moiety, additional biological particles are excluded from being retained.

Conditions under which cell contacting with a surface containing capture moieties is performed can be used to select, for example, cells with higher relative binding affinity for a particular ligand than other cells. For example, the cell contacting step can be performed in the presence of inhibitors and/or competitors of the binding. For cells that are bound and retained by the disclosed systems, forces can be applied to the cells such that some cells, cells with lower binding affinity for example, are released from the substrate. In some examples, mechanical forces may be applied to the cells. In some examples, shear forces may be applied to the cells.

Biological particles (e.g., cells or nuclei) retained on the substrates disclosed here may be examined visually and/or using imaging. The biological particles may be stained with dyes, antibodies, and/or other probes prior to the imaging or visualization. Information obtained through these methods may add to other information obtained using the disclosed methods, or may be used in a stand-alone fashion, or in a preliminary way to monitor the biological particle binding steps of the disclosed methods.

Processing of Analytes from Biological Particles

Biological particles (e.g., cells or nuclei) that bind to capture regions of the substrate and that are retained there may be caused to release analytes. In some examples, the biological particles may be contacted with substances, detergents or mild detergents for example, to disrupt membranes, resulting in release of analytes from the retained biological particles. In some examples, the released analytes diffuse away from the biological particle and contact barcode molecules associated with the capture moieties that bound the biological particles from which the analytes originated. In instances where the analytes contact a barcode molecule having a analyte binding sequence capable of binding that analyte, the analyte is bound by the barcode molecule.

In some examples, the analytes bound by analyte binding sequences of barcode molecules are nucleic acid molecules. In some examples, the nucleic acid molecules may be DNA or RNA molecules. In some examples, the nucleic acid molecules may be mRNA molecules. In some examples the analytes bound by analyte binding sequences may be nucleic acid molecules that are complements of and/or amplification products of analytes that are DNA, RNA or mRNA.

In some examples, the analyte of interest is mRNA and hybridization occurs via capture of mRNA from the captured single biological particle (e.g., cell or nucleus) by an analyte binding sequence (i.e., capture domain) involving a reverse transcription of the mRNA and the oligonucleotide domain of the reverse transcription primer to yield cDNA, which can then be analyzed. The hybridization can proceed using techniques that are known from the field of spatial transcriptomics. A detailed description of one suitable hybridization protocol and subsequent analysis is provided in the Visium Spatial Gene Expression Reagent Kits User Guide, Rev. A, published by 10X Genomics, which is incorporated herein by reference. The methods allow for molecular barcoding and/or imaging analysis of a large number of single immobilized biological particles (e.g., cells or nuclei) simultaneously on a single slide surface.

In some examples, a plurality of molecules are generated from barcoded molecules that have bound analytes. Generally, the generated molecules contain copies of the barcodes or barcode sequences contained in the barcode molecules. This may be done enzymatically, in some examples using reverse transcriptases and polymerases. Libraries may be created using the generated molecules. Nucleotide sequences of the libraries may be obtained.

In some examples, the nucleotide sequences obtained from the libraries may be analyzed. In some examples, the analysis may correlate an identity of a cell capture moiety (e.g., amino acid sequence of a peptide in a cell capture moiety) with specific nucleotide sequences obtained from the library (e.g., sequences of TCRs, subunits of TCRs, BCRs, chains of BCRs).

Kits

Also provided herein are kits. The kits may contain all or part of the systems disclosed in this application. The kits may contain one or more reagents that can be used in various embodiments of methods that use the systems. In some examples, a kit may contain a system as disclosed herein, and one or more of a cell dye, a cell stain and/or an antibody. In some examples, the kit may contain reagents that affect cell binding and/or retention by the systems disclosed in this application. For example, the kit may contain an inhibitor of cell binding to a cell capture moiety that is part of the system. The kit may contain a competitor for cell binding to a cell capture moiety that is part of the system.

EMBODIMENTS

Some example embodiments of the invention are disclosed in the numbered paragraphs below. Example embodiments are also disclosed in the Claims of this disclosure.

1. A method for processing a nucleic acid molecule, said method comprising:
   (a) providing a support comprising a plurality of spatially isolated nucleic acid barcode molecules and a plurality of spatially isolated antigens, wherein a nucleic acid barcode molecule of said plurality of nucleic acid barcode molecules comprises a spatial barcode sequence, and wherein said nucleic acid barcode molecule is co-localized with an antigen of said plurality of spatially isolated antigens;
   (b) contacting said support with a membrane bound biological particle comprising (i) a nucleic acid molecule comprising a target sequence and (ii) an antigen binding protein under conditions sufficient for said antigen binding protein to bind to said antigen; and
   (c) disrupting a membrane of said membrane bound biological particle to contact said nucleic acid molecule of said membrane bound biological particle with said nucleic acid barcode molecule under conditions sufficient for coupling said nucleic acid molecule to said nucleic acid barcode molecule.
2. The method of embodiment 1, wherein said nucleic acid barcode molecule comprises a capture sequence configured to hybridize to said nucleic acid molecule.
3. The method of embodiment 1, wherein said membrane bound biological particle is a cell, virus, or nucleus.
4. The method of embodiment 3, wherein said membrane bound biological particle is a cell, and wherein said cell is a B cell.
5. The method of embodiment 3, wherein said membrane bound biological particle is a cell, and wherein said cell is a T cell.
6. The method of embodiment 1, wherein said nucleic acid molecule comprises a messenger ribonucleic acid (mRNA).
7. The method of embodiment 6, wherein said mRNA encodes said antigen binding protein.
8. The method of embodiment 1, wherein said antigen binding protein is a T cell receptor.
9. The method of embodiment 1, wherein said antigen binding protein is a B cell receptor.
10. The method of embodiment 1, wherein said plurality of spatially isolated nucleic acid barcode molecules comprises at least 100 nucleic acid barcode molecules.
11. The method of embodiment 1, wherein said plurality of spatially isolated nucleic acid barcode molecules comprises at least 1,000 nucleic acid barcode molecules.
12. The method of embodiment 1, wherein said plurality of spatially isolated nucleic acid barcode molecules comprises at least 10,000 nucleic acid barcode molecules.
13. The method of embodiment 1, wherein said spatially isolated nucleic acid barcode molecule is at least 50 μm from a second spatially isolated nucleic acid barcode molecule of said plurality of spatially isolated nucleic acid barcode molecules.
14. The method of embodiment 1, wherein said spatially isolated nucleic acid barcode molecule is at least 100 μm from a second spatially isolated nucleic acid barcode molecule of said plurality of spatially isolated nucleic acid barcode molecules.
15. The method of embodiment 1, wherein said spatial barcode sequence is different than a second spatial barcode sequence of a second spatially isolated nucleic acid barcode molecule of said plurality of spatially isolated nucleic acid barcode molecules.
16. The method of embodiment 1, wherein said spatially isolated nucleic acid barcode molecule comprises a unique molecular identifier.
17. The method of embodiment 1, wherein said antigen is an antigen bound dextramer.
18. The method of embodiment 1, wherein said antigen is different than a second antigen of said plurality of spatially isolated antigens.
19. The method of embodiment 1, wherein said antigen is at least 50 μm from a second antigen of said plurality of spatially isolated antigens.
20. The method of embodiment 1, wherein said antigen is at least 100 μm from a second antigen of said plurality of spatially isolated antigens.
21. The method of embodiment 2, wherein said capture sequence is a VDJ specific capture sequence.
22. The method of embodiment 1, wherein said spatially isolated nucleic acid barcode molecule of said plurality of spatially isolated nucleic acid barcode molecules is within 7 μm of said spatially isolated antigen.
23. The method of embodiment 1, wherein said spatially isolated nucleic acid barcode molecule of said plurality of spatially isolated nucleic acid barcode molecules is within 1 μm of said spatially isolated antigen.
24. The method of embodiment 1, wherein said spatially isolated nucleic acid barcode molecule of said plurality of spatially isolated nucleic acid barcode molecules is within 0.5 μm of said spatially isolated antigen.
25. The method of embodiment 1, wherein said spatially isolated nucleic acid barcode molecule of said plurality of spatially isolated nucleic acid barcode molecules is within 0.1 μm of said spatially isolated antigen.
26. The method of embodiment 1, wherein said disrupting comprises permeabilizing said membrane of said membrane bound biological particle.
27. The method of embodiment 26, wherein said membrane is a cell membrane.
28. The method of embodiment 1, wherein said disrupting comprises lysing said membrane bound biological particle.

29. The method of embodiment 1, further comprising coupling said nucleic acid molecule and said nucleic acid barcode molecule to generate a barcoded nucleic acid molecule comprising (i) said target sequence or complement thereof and (ii) said spatial barcode sequence or complement thereof.

30. The method of embodiment 29, further comprising sequencing said barcoded nucleic acid molecule.

31. The method of embodiment 29, further comprising using reverse transcription to generate said barcoded nucleic acid molecule.

32. The method of embodiment 1, further comprising, prior to (c), applying a force to dissociate a second membrane bound biological particle from said support.

33. The method of embodiment 32, wherein said force is from a flow of a liquid.

34. The method of embodiment 32, wherein said second membrane bound biological particle interacts with antigen of said plurality of spatially isolated antigens with a $K_d$ greater than 10-8.

35. The method of embodiment 32, wherein said second membrane bound biological particle interacts with antigen of said plurality of spatially isolated antigens with a $K_d$ greater than 10-7.

36. The method of embodiment 32, wherein said second membrane bound biological particle interacts with antigen of said plurality of spatially isolated antigens with a $K_d$ greater than 10-6.

37. The method of embodiment 1, further comprising, prior to (c), performing microscopic analysis of said membrane bound biological particle.

38. The method of embodiment 37, wherein said performing microscopic analysis comprises contacting said membrane bound biological particle with a cell surface marker detection agent.

39. The method of embodiment 38, wherein said cell surface marker detection agent is an antibody configured to couple to a cell surface marker.

40. The method of embodiment 1, wherein said membrane bound biological particle further comprises a gene, and wherein said method further comprises determining presence or absence of expression of gene.

41. The method of embodiment 1, wherein said membrane bound biological particle further comprise a gene, and wherein said method further comprises determining presence or absence of expression of a protein encoded by said gene.

42. A system for processing a nucleic acid molecule, comprising:
a support comprising a plurality of spatially isolated regions, wherein said plurality of spatially isolated regions is configured to contain a plurality of spatially isolated nucleic acid barcode molecules and a plurality of spatially isolated antigens, wherein a barcoded oligonucleotide of said plurality of barcoded oligonucleotides comprises a spatial barcode sequence and a capture sequence, and wherein said barcoded oligonucleotide is co-localized with an antigen of said a plurality of spatially isolated antigens; and
one or more computer processors that are individually or collectively programmed to:
(a) direct said support to be brought in contact with a membrane bound biological particle comprising a nucleic acid molecule and an antigen binding protein under conditions sufficient for said antigen binding protein to bind to said antigen; and
(b) direct disruption of a membrane of said membrane bound biological particle to permit said nucleic acid molecule of said membrane bound biological particle to come in contact with said nucleic acid barcode molecule under conditions sufficient for binding said nucleic acid molecule to said capture sequence to capture said nucleic acid barcode molecule on said support.

43. The system of embodiment 42, wherein said membrane bound biological particle is a cell, virus, or nucleus.

44. The system of embodiment 43, wherein said membrane bound biological particle is a cell, wherein said cell is a B cell.

45. The system of embodiment 43, wherein said membrane bound biological particle is a cell, wherein said cell is a T cell.

46. The system of embodiment 42, wherein said nucleic acid molecule comprises a messenger ribonucleic acid (mRNA).

47. The method of embodiment 46, wherein said mRNA is an mRNA transcript for said antigen binding protein.

48. The system of embodiment 42, wherein said antigen binding protein is a T cell receptor.

49. The system of embodiment 42, wherein said antigen binding protein is a B cell receptor.

50. The system of embodiment 42, wherein said plurality of spatially isolated nucleic acid barcode molecules comprises at least 100 nucleic acid barcode molecules.

51. The system of embodiment 42, wherein said plurality of spatially isolated nucleic acid barcode molecules comprises at least 1,000 nucleic acid barcode molecules.

52. The system of embodiment 42, wherein said plurality of spatially isolated nucleic acid barcode molecules comprises at least 10,000 nucleic acid barcode molecules.

53. The system of embodiment 42, wherein said spatially isolated nucleic acid barcode molecule is at least 50 μm from a second spatially isolated nucleic acid barcode molecule of said plurality of spatially isolated nucleic acid barcode molecules.

54. The system of embodiment 42, wherein said spatially isolated nucleic acid barcode molecule is at least 100 μm from a second spatially isolated nucleic acid barcode molecule of said plurality of spatially isolated nucleic acid barcode molecules.

55. The system of embodiment 42, wherein said spatial barcode sequence is different than a second spatial barcode sequence of a second spatially isolated nucleic acid barcode molecule.

56. The system of embodiment 42, wherein said spatially isolated nucleic acid barcode molecule comprises a unique molecular identifier.

57. The system of embodiment 42, wherein said antigen is an antigen bound dextramer.

58. The system of embodiment 42, wherein said antigen is different than a second antigen of said plurality of spatially isolated antigens.

59. The system of embodiment 42, wherein said antigen is at least 50 μm from a second antigen of said plurality of spatially isolated antigens.

60. The system of embodiment 42, wherein said antigen is at least 100 μm from a second antigen of said plurality of spatially isolated antigens.

61. The system of embodiment 42, wherein said capture sequence is a VDJ specific capture sequence.

62. The system of embodiment 42, wherein said spatially isolated nucleic acid barcode molecule of said plurality of spatially isolated nucleic acid barcode molecules is within 7 μm of said spatially isolated antigen.
63. The system of embodiment 42, wherein said spatially isolated nucleic acid barcode molecule of said plurality of spatially isolated nucleic acid barcode molecules is within 1 μm of said spatially isolated antigen.
64. The system of embodiment 42, wherein said spatially isolated nucleic acid barcode molecule of said plurality of spatially isolated nucleic acid barcode molecules is within 0.5 μm of said spatially isolated antigen.
65. The system of embodiment 42, wherein said spatially isolated nucleic acid barcode molecule of said plurality of spatially isolated nucleic acid barcode molecules is within 0.1 μm of said spatially isolated antigen.
66. The system of embodiment 42, wherein said disruption comprises permeabilization of said membrane of said membrane bound biological particle.
67. The system of embodiment 66, wherein said membrane is a cell membrane.
68. The system of embodiment 42, wherein said disruption comprises lysing said membrane bound biological particle.
69. The system of embodiment 42, wherein said one or more computer processors are further individually or collectively programmed to: direct coupling of said nucleic acid molecule and said nucleic acid barcode molecule to generate a barcoded nucleic acid molecule comprising (i) said target sequence or complement thereof and (ii) said spatial barcode sequence or complement thereof.
70. The system of embodiment 69, wherein said one or more computer processors are further individually or collectively programmed to: direct sequencing of said barcoded nucleic acid molecule.
71. The system of embodiment 69, wherein said one or more computer processors are further individually or collectively programmed to: direct reverse transcription to generate said barcoded nucleic acid molecule.
72. The system of embodiment 42, wherein said one or more computer processors are further individually or collectively programmed to, prior to (b), direct a force to dissociate a second membrane bound biological particle from said support.
73. The system of embodiment 72, wherein said force is from a flow of a liquid.
74. The system of embodiment 72, wherein second membrane bound biological particle interacts with antigen of said plurality of spatially isolated antigens with a Kd greater than 10-8.
75. The system of embodiment 72, wherein said second membrane bound biological particle interacts with an antigen of said plurality of spatially isolated antigens with a Kd greater than 10-7.
76. The system of embodiment 72, wherein said second membrane bound biological particle interacts with an antigen of said plurality of spatially isolated antigens with a Kd greater than 10-6.
77. The system of embodiment 42, wherein said one or more computer processors are further individually or collectively programmed to, prior to (b), direct microscopic analysis of said membrane bound biological particle.
78. The system of embodiment 77, wherein said microscopic analysis comprises contacting said membrane bound biological particle with a cell surface marker detection agent.
79. The system of embodiment 78, wherein said cell surface marker detection agent is an antibody configured to couple a cell surface marker.
80. The system of embodiment 42, wherein said membrane bound biological particle further comprises a gene, and wherein said one or more computer processors are further individually or collectively programmed to direct determination of a presence or absence of expression of said gene.
81. The system of embodiment 42, wherein said membrane bound biological particle further comprise a gene, wherein said one or more computer processors are further individually or collectively programmed to direct determination of a presence or absence of expression of a protein encoded by said gene.
82. A support comprising a plurality of spatially isolated nucleic acid barcode molecules and a plurality of spatially isolated antigens;
wherein a spatially isolated nucleic acid barcode molecule of said plurality of spatially isolated nucleic acid barcode molecules comprises a spatial barcode sequence and a capture sequence, and
wherein said spatially isolated nucleic acid barcode molecule is colocalized with an antigen of said plurality of antigens.
83. The support of embodiment 82, wherein said spatially isolated nucleic acid barcode molecule and said antigen are not physically coupled.
84. The support of embodiment 82, wherein said spatially isolated barcoded nucleic molecule further comprises a unique molecular identifier.
85. The support of embodiment 82, wherein said plurality of spatially isolated nucleic acid barcode molecules comprises at least 100 nucleic acid barcode molecules.
86. The support of embodiment 82, wherein said plurality of spatially isolated nucleic acid barcode molecules comprises at least 1,000 nucleic acid barcode molecules.
87. The support of embodiment 82, wherein said plurality of spatially isolated nucleic acid barcode molecules comprises at least 10,000 nucleic acid barcode molecules.
88. The support of embodiment 82, wherein said spatially isolated nucleic acid barcode molecule is at least 50 μm from a second spatially isolated nucleic acid barcode molecule of said plurality of spatially isolated nucleic acid barcode molecules.
89. The support of embodiment 82, wherein said spatially isolated nucleic acid barcode molecule is at least 100 μm from a second spatially isolated nucleic acid barcode molecule of said plurality of spatially isolated nucleic acid barcode molecules.
90. The support of embodiment 82, wherein said spatial barcode sequence is different than a second spatial barcode sequence of a second spatially isolated nucleic acid barcode molecule of said plurality of spatially isolated antigens.
91. The support of embodiment 82, wherein said antigen is an antigen bound dextramer.
92. The support of embodiment 82, wherein said antigen is different than a second antigen of said plurality of spatially isolated antigens.

93. The support of embodiment 82, wherein said antigen is at least 50 μm from a second antigen of said plurality of spatially isolated antigens.
94. The support of embodiment 82, wherein said antigen is at least 100 μm from a second antigen of said plurality of spatially isolated antigens.
95. The support of embodiment 82, wherein said capture sequence is a VDJ specific capture sequence.
96. The support of embodiment 82, wherein said spatially isolated nucleic acid barcode molecule of said plurality of spatially isolated nucleic acid barcode molecules is within 7 μm of said spatially isolated antigen.
97. The support of embodiment 82, wherein said spatially isolated nucleic acid barcode molecule of said plurality of spatially isolated nucleic acid barcode molecules is within 1 μm of said spatially isolated antigen.
98. The support of embodiment 82, wherein said spatially isolated nucleic acid barcode molecule of said plurality of spatially isolated nucleic acid barcode molecules is within 0.5 μm of said spatially isolated antigen.
99. The support of embodiment 82, wherein said spatially isolated nucleic acid barcode molecule of said plurality of spatially isolated nucleic acid barcode molecules is within 0.1 μm of said spatially isolated antigen.
100. A system, comprising:
a substrate;
a cell capture moiety attached to the substrate; and
a plurality of barcode molecules, associated with the cell capture moiety, the barcode molecules comprising;
a common barcode sequence; and
an analyte binding sequence.
101. The system of embodiment 100, wherein the substrate comprises glass or plastic.
102. The system of one of embodiments 100 or 101, wherein the substrate is a substantially planar substrate.
103. The system of any one of embodiments 100-102, wherein the substrate is free of microwells.
104. The system of any one of embodiments 100-103, wherein the substrate is coated or modified to accept attachment of the cell capture moiety and/or the plurality of barcode molecules.
105. The system of any one of embodiments 100-104, wherein multiple cell capture moieties are attached to the substrate, the barcode molecules associated with each of the multiple cell capture moieties having a different common barcode sequence.
106. The system of embodiment 105, wherein the multiple cell capture moieties are arranged on the substrate to prevent diffusion of an analyte from a cell bound by one cell capture moiety to another or adjacent cell capture moiety.
107. The system of any one of embodiments 100-106, wherein the cell capture moiety comprises a substance to which a cell can bind.
108. The system of any one of embodiments 100-107, wherein the cell capture moiety comprises a substance to which a specific cell type can bind and other cell types cannot bind.
109. The system of any one of embodiments 100-108, wherein the cell capture moiety comprises a protein, polysaccharide, lipid and/or nucleic acid.
110. The system of any one of embodiments 100-109, wherein the cell capture moiety comprises molecules to which a cell from the immune system can bind.
111. The system of any one of embodiments 100-110, wherein the cell capture moiety comprises molecules to which a lymphocyte, mononuclear phagocyte, dendritic cell or granulocyte can bind.
112. The system of any one of embodiments 100-111, wherein the cell capture moiety comprises molecules to which a T-cell lymphocyte or a B-cell lymphocyte can bind.
113. The system of any one of embodiments 100-112, wherein the cell capture moiety comprises a ligand for a cellular receptor.
114. The system of any one of embodiments 100-113, wherein the cell capture moiety comprises a ligand for a T-cell receptor (TCR) or B-cell receptor (BCR).
115. The system of any one of embodiments 100-114, wherein the cell capture moiety comprises a peptide having 5, 6, 7, 8, 9, 10, 11, 12, 13, 14, 15, 16, 17, 18, 19, 20, 21, 22, 23, 24, 25, 26, 27 or 28 amino acids.
116. The system of any one of embodiments 100-115, wherein the cell capture moiety comprises a major histocompatibility complex (MHC) molecule.
117. The system of any one of embodiments 100-116, where the cell capture moiety comprises a major histocompatibility complex class I (MHC-I) molecule or a major histocompatibility complex class II (MHC-II) molecule
118. The system of any one of embodiments 100-117, wherein the cell capture moiety comprises an MHC multimer.
119. The system of any one of embodiments 100-118, wherein the cell capture moiety comprises at least two different molecules.
120. The system of any one of embodiments 100-119, wherein the cell capture moiety comprises a peptide and another molecule.
121. The system of any one of embodiments 100-120, wherein the cell capture moiety comprises a peptide and a major histocompatibility complex (MHC) molecule.
122. The system of any one of embodiments 100-121, where the cell capture moiety comprises a peptide and a major histocompatibility complex class I (MHC-I) molecule or a major histocompatibility complex class II (MHC-II) molecule.
123. The system of any one of embodiments 100-122, wherein the cell capture moiety comprises a peptide and an MHC multimer.
124. The system of embodiment any one of embodiments 100-123, wherein the cell capture moiety is cell free.
125. The system of embodiment any one of embodiments 100-124, wherein the plurality of barcode molecules are attached to the substrate.
126. The system of any one of embodiments 100-125, wherein the plurality of barcode molecules associated with a cell capture moiety are attached to the substrate and within about 1 to 100 μm of the cell capture moiety.
127. The system of any one of embodiments 100-126, wherein the analyte binding sequence of the barcode molecules is configured to bind one or more molecules from a cell captured by or bound to the cell capture moiety.
128. The system of any one of embodiments 100-127, wherein the analyte binding sequence of the barcode molecules is configured to bind specific proteins, polysaccharides, lipids and/or nucleic acids.
129. The system of embodiment any one of embodiments 100-128, wherein the analyte binding sequence of the barcode molecules comprises a nucleotide sequence complementary to a nucleic acid molecule, the complement of the nucleic acid molecule, or amplification product thereof, from a cell captured by or bound to the cell capture moiety.

130. The system of any one of embodiments 100-129, wherein the analyte binding sequence of the barcode molecules comprises a nucleotide sequence complementary to an RNA, a complement of an RNA, or amplification product of an RNA, from a cell captured by or bound to the cell capture moiety.

131. The system of any one of embodiments 100-130, wherein the analyte binding sequence of the barcode molecules comprises a nucleotide sequence complementary to an RNA, a complement of an RNA, or amplification product of an RNA, that encodes a rearranged V(D)J sequence of a T-cell receptor (TCR) or a B-cell receptor (BCR) from a cell captured by or bound to the cell capture moiety.

132. The system of any one of embodiments 100-131, wherein the analyte binding sequence of the barcode molecules comprises a V(D)J-specific capture sequence.

133. The system of any one of embodiments 100-132, wherein different barcode molecules of the plurality of barcode molecules are capable of binding different analytes.

134. The system of any one of embodiments 100-133, wherein different barcode molecules of the plurality of barcode molecules have different analyte binding sequences.

135. The system of any one of embodiments 100-134, wherein different barcode molecules of the plurality of barcode molecules are capable of binding RNAs, complements or amplification products thereof, having different sequences.

136. The system of any one of embodiments 100-135, wherein different barcode molecules of the plurality of barcode molecules that are configured to bind the same or related analyte, comprise a second barcode sequence, common to the same or related analyte bound, and different than the common barcode sequence of embodiment 1.

137. The system of any one of embodiments 100-136, wherein different barcode molecules of the plurality of barcode molecules, comprise a third barcode sequence, different for each barcode molecule, and different from the common barcode sequence of embodiment 1, and the second barcode sequence of embodiment 136.

138. A system, comprising:
a substrate comprising a plurality of cell capture regions, wherein a cell capture region comprises;
a cell capture moiety; and
a plurality of barcode molecules, wherein the plurality of barcode molecules comprise a common barcode sequence and an analyte binding sequence.

139. The system of embodiment 138, wherein a substrate comprises between about $10^3$ and $10^8$ cell capture regions.

140. The system of one of embodiments 138 or 139, wherein a cell capture region is between about 10 and $10^3$ µm across.

141. The system of any one of embodiments 138-140, wherein a distance between adjacent cell capture regions is between about 1 and $10^2$ µm.

142. The system any one of embodiments 138-141, wherein a cell capture region comprises between about $10^3$ and $10^9$ barcode molecules.

143. The system of any one of embodiments 138-142, wherein the cell capture moiety is configured to capture one cell, or more than one identical cells.

144. The system of any one of embodiments 138-143, wherein the plurality of cell capture regions are configured to capture immune system cells.

145. The system of any one of embodiments 138-144, wherein the plurality of cell capture regions are configured to capture T-cell lymphocytes or B-cell lymphocytes.

146. The system of any one of embodiments 138-145, wherein the plurality of cell capture regions are configured to bind to or be bound by a B-cell receptor (BCR) that is part of a B-cell lymphocyte.

147. The system of any one of embodiments 138-146, wherein the plurality of cell capture regions comprise cell capture moieties comprising antigens or parts of antigens capable of being bound by B-cell receptors or CDR regions of a B-cell lymphocyte.

148. The system of any one of embodiments 138-147, wherein the analyte binding sequences of the plurality of barcode molecules are configured to bind cellular analytes comprising rearranged V(D)J sequences encoding a B-cell receptor (BCR).

149. The system of any one of embodiments 138-148, wherein the analyte binding sequences of the plurality of barcode molecules comprise a V(D)J-specific capture sequence.

150. The system of any one of embodiments 138-145, wherein the plurality of cell capture regions are configured to capture $CD4^+$ T-cell lymphocytes or $CD8^+$ T-cell lymphocytes.

151. The system of any one of embodiments 138-145 and 150, wherein the plurality of cell capture regions are configured to bind to or be bound by a T-cell receptor (TCR), TCRα subunit, TCRβ subunit, or one or more CDR regions of TCRα and/or TCRβ subunits, that are part of a T-cell lymphocyte.

152. The system of any one of embodiments 138-145 and 150-151, wherein the plurality of cell capture regions comprise cell capture moieties comprising a peptide.

153. The system of any one of embodiments 138-145 and 150-152, wherein the plurality of cell capture regions comprise cell capture moieties comprising a peptide and a major histocompatibility complex class I (MHC-I) molecule or a major histocompatibility complex class II (MHC-II) molecule.

154. The system of any one of embodiments 138-145 and 150-153, wherein the plurality of cell capture regions comprise cell capture moieties comprising a peptide and an MHC multimer.

155. The system of any one of embodiments 138-145 and 150-154, wherein the analyte binding sequences of the plurality of barcode molecules are configured to bind cellular analytes comprising rearranged V(D)J sequences encoding a T-cell receptor (TCR), TCRα subunit or TCRβ subunit.

156. The system of any one of embodiments 138-145 and 150-155, wherein the analyte binding sequences of the plurality of barcode molecules comprise a V(D)J-specific capture sequence.

157. The system of any one of embodiments 138-156, wherein the analyte binding sequences of the plurality of barcode molecules are configured to bind cellular analytes with changed levels and/or expression as a result of a B-cell receptor (BCR) of a B-cell lymphocyte binding to an antigen, or a T-cell receptor (TCR)

of a T-cell lymphocyte binding to a peptide or to a peptide in the context of an MHC-I or MHC-II molecule.

158. A system comprising:
a substrate comprising a plurality of cell capture regions configured to capture a B-cell lymphocyte, wherein a cell capture region comprises;
a cell capture moiety comprising an antigen to which a B-cell receptor (BCR) can bind; and
a plurality of barcode molecules in proximity to the cell capture moiety, wherein the plurality of barcode molecules comprise;
a common barcode sequence; and
a nucleotide capture sequence capable of binding an RNA, or amplification product thereof, that encodes a rearranged V(D)J sequence of a BCR.

159. A system comprising:
a substrate comprising a plurality of cell capture regions configured to capture a T-cell lymphocyte, wherein a cell capture region comprises;
a cell capture moiety comprising a peptide and a major histocompatibility complex class I (MHC-I) molecule and/or a major histocompatibility complex class II (MHC-II) molecule and
a plurality of barcode molecules in proximity to the cell capture moiety, wherein the plurality of barcode molecules comprise;
a common barcode sequence; and
a nucleotide capture sequence capable of binding an RNA, or amplification product thereof, that encodes a rearranged V(D)J sequence of a TCR, a TCRα subunit or a TCRβ subunit.

160. A method of making the system of any one of embodiments 100-159, comprising:
printing molecules comprising the cell capture moieties to the substrate; and
printing the plurality of barcode molecules to the substrate.

161. A method, comprising:
contacting cells in a population with the cell capture moieties of the system of any one of embodiments 100-159, to retain in place a subpopulation of cells that binds to the cell capture moieties; and
releasing analytes from the retained cells such that the analytes contact barcode molecules closest to the cell capture moiety to which the cell has bound, to bind released analytes to barcode molecules having an analyte binding sequence specific for the released analyte.

162. The method of embodiment 161, wherein cells in the population are contacted with the cell capture moieties by flowing the cells in the population over the substrate.

163. The method of one of embodiments 6161-162, wherein cells in the population are contacted with the cell capture moieties under conditions such that cells having a relatively stronger affinity for the cell capture moieties are retained and cells having a relatively weaker affinity for the cell capture moieties are not retained.

164. The method of any one of embodiments 161-163, wherein cells in the population are contacted with the cell capture moieties in the presence of one or more molecules that inhibit cell binding or compete with cells for binding to the cell capture moieties.

165. The method of any one of embodiments 161-164, wherein a force is applied to cells retained in place on the cell capture moieties such that cells having a relatively weaker affinity for the cell capture moieties are not retained.

166. The method of embodiment 165, wherein the force applied to the cells is a mechanical force, including a shear mechanical force.

167. The method of any one of embodiments 161-166, wherein analytes are released from the retained cells by permeabilizing the retained cells.

168. The method of any one of embodiments 161-167, wherein the cell capture moieties comprise ligands for specific molecules on surfaces of at least some cells in the population.

169. The method of any one of embodiments 161-168, wherein the cell capture moieties comprise ligands for a T-cell receptor (TCR) or a B-cell receptor (BCR).

170. The method of any one of embodiments 161-169, wherein the cells in the population are fixed.

171. The method of embodiment 170, comprising subsequent to contacting the fixed cells with the cell capture moieties to retain the subpopulation in place, the step of reversing fixation of the fixed cells.

172. The method of any one of embodiments 161-171, comprising the step of generating a plurality of molecules from barcoded molecules that have bound a released analyte, the plurality of molecules generated comprising the common barcode sequence, or complement thereof, and a nucleotide sequence corresponding to the bound analyte.

173. The method of embodiment 172, comprising the step of obtaining a nucleotide sequence of the plurality of molecules generated from the barcoded molecules that have bound a released analyte.

174. The method of embodiment 173, comprising the step of correlating an identity of a cell capture moiety with one or more of the nucleotide sequences generated from barcoded molecules that bound an analyte released from the cell bound by the cell capture moiety.

175. The method of embodiment 174, wherein an identity of a peptide from a cell capture moiety is correlated with a nucleotide sequence generated from barcoded molecules that bound an analyte comprising a rearranged V(D)J nucleotide sequence.

176. The method of any one of embodiments 161-175, comprising, the step of staining, labeling and/or visualizing cells retained in place on the cell capture moieties.

177. A method, comprising:
providing a system, comprising;
a substrate comprising a plurality of cell capture regions, wherein a cell capture region comprises;
a cell capture moiety; and
a plurality of barcode molecules, wherein the plurality of barcode molecules comprise a common barcode sequence and an analyte binding sequence;
flowing a population of cells over the substrate to select T-cell or B-cell lymphocytes from the population of cells and bind the lymphocytes to the cell capture moieties;
permeabilizing the lymphocytes bound to the cell capture moieties to release a plurality of analytes from the cells, such that diffusion of the analytes is substantially confined to the cell capture region containing the bound cell, and analytes comprising rearranged V(D)J sequences encoding a T-cell receptor (TCR), TCRα subunit, TCRβ subunit, or a B-cell receptor (BCR), or subunit therefrom, are bound by barcode molecules having analyte binding sequences specific for those receptors or subunits; and generating a plurality of molecules from the barcode molecules that have bound the rearranged V(D)J sequences, the plurality of molecules generated comprising the common barcode sequence, or complement thereof, and a nucleotide sequence corresponding to the bound analyte.

178. The method of embodiment 177, wherein the cell capture moieties comprise ligands for a T-cell receptor (TCR) or a B-cell receptor (BCR).

179. The method of one of embodiments 177-178, wherein the cell capture moieties comprise a peptide, polypeptide or protein capable of being bound by a T-cell receptor (TCR), B-cell receptor or subunits thereof, and a major histocompatibility complex class I (MHC-I) molecule and/or a major histocompatibility complex class II (MHC-II) molecule.

180. The method of embodiment 179, wherein the MHC-I and/or MHC-II molecules comprise MHC multimers.

181. The method of one of embodiments 179-180, wherein the MHC-I and/or MHC-II molecules are MHC-matched-matched to the population of cells flowed over the substrate.

182. The method of any one of embodiments 179-180, comprising the step of obtaining the nucleotide sequence of the plurality of molecules generated from the barcoded molecules that have bound the rearranged V(D)J sequences.

183. The method of embodiment 182, comprising the step of correlating an identity of a cell capture moiety and/or lymphocyte bound thereby, with one or more of the nucleotide sequences generated from barcoded molecules that bound analytes comprising rearranged V(D)J sequences released from the lymphocyte bound by the cell capture moiety.

184. A kit, comprising:
a system of any one of embodiments 100-159; and one or more of a cell dye, a cell stain, an antibody, an inhibitor of cell binding to a cell capture moiety, and a competitor for cell binding to a cell capture moiety.

The invention claimed is:

1. A method comprising:
providing a substrate comprising a plurality of capture regions, wherein a capture region of the plurality of capture regions comprises:
a plurality of cell binding ligands affixed to the substrate, wherein a cell binding ligand of the plurality of cell binding ligands binds to a cell surface receptor, wherein each of the cell binding ligands is at least 100 microns from each other on the substrate; and
a plurality of nucleic acid barcode molecules affixed to the substrate, wherein each nucleic acid barcode molecule of the plurality of nucleic acid barcode molecules includes a common barcode sequence, wherein the common barcode sequence is unique to the capture region and an analyte binding sequence, wherein the plurality of the nucleic acid barcode molecules are within 1 to 100 microns of each cell binding ligand on the substrate;

contacting a plurality of cells each comprising the cell surface receptor with the substrate, wherein a subpopulation of the cells of the plurality of cells binds to the cell binding ligand of the plurality of cell binding ligands, thereby generating a captured cell subpopulation that binds the cell binding ligand at the capture region;

releasing a plurality of nucleic acid analytes from each of the captured cells of the captured subpopulation at the capture region to allow contact with the nucleic acid barcode molecules in proximity of the cell binding ligand and hybridizing the nucleic acid analytes of the plurality of nucleic acid analytes to the nucleic acid barcode molecules; and forming a plurality of nucleic acid barcoded molecules from the plurality of nucleic acid analytes and the plurality of nucleic acid barcode molecules comprising extending the nucleic acid barcode molecule with a reverse transcriptase or a polymerase following hybridization, wherein each formed nucleic acid barcoded molecule of the plurality of nucleic acid barcoded molecules includes the common barcode sequence, or a complement thereof, and a sequence corresponding to the nucleic acid analyte, or a complement thereof.

2. The method of claim 1, wherein the plurality of cells is a plurality of fresh or unfixed cells.

3. The method of claim 1, wherein the plurality of cells comprise T cells and/or B cells.

4. The method of claim 1, wherein the analyte binding sequence comprises a nucleotide sequence complementary to a ribonucleic acid (RNA) molecule, a reverse complement of an RNA molecule, or amplification product of an RNA molecule, that encodes a rearranged V(D)J sequence of a T-cell receptor (TCR) or a B-cell receptor (BCR) from the captured cell.

5. The method of claim 1, wherein the plurality of nucleic acid analytes comprise messenger RNA (mRNA).

6. The method of claim 1, wherein the cell surface receptor is a T-cell receptor (TCR) or a B-cell receptor (BCR).

7. The method of claim 1, wherein the analyte binding sequence comprises a poly(T) sequence.

8. The method of claim 1, wherein releasing the plurality of nucleic acid analytes from each of the captured cells comprises lysing the captured cells.

9. The method of claim 1, wherein the nucleic acid barcode molecule further comprises a unique molecular identifier.

10. The method of claim 1, wherein releasing the plurality of nucleic acid analytes from each of the captured cells at the capture region comprises permeabilization.

11. The method of claim 1, further comprising determining the sequence of the common barcode sequence, or a complement thereof, and all or a portion of the nucleic acid analyte, or a complement thereof.

* * * * *